United States Patent
McDonnell et al.

(10) Patent No.: US 9,943,351 B2
(45) Date of Patent: Apr. 17, 2018

(54) WOVEN RETENTION DEVICES, SYSTEMS, PACKAGING, AND RELATED METHODS

(71) Applicant: Woven Orthopedic Technologies, LLC, Manchester, CT (US)

(72) Inventors: Christopher McDonnell, Sandy Hook, CT (US); Robert L. Richards, Hamden, CT (US); Nicole S. Sroka, Derby, CT (US); Ernest N. Corrao, Jr., Bethel, CT (US); Ronald G. Litke, Jr., Sandy Hook, CT (US)

(73) Assignee: Woven Orthopedic Technologies, LLC, Manchester, CT (US)

( * ) Notice: Subject to any disclaimer, the term of this patent is extended or adjusted under 35 U.S.C. 154(b) by 587 days.

(21) Appl. No.: 14/487,951

(22) Filed: Sep. 16, 2014

(65) Prior Publication Data
US 2016/0074072 A1 Mar. 17, 2016

(51) Int. Cl.
| | | |
|---|---|---|
| A61B 17/88 | (2006.01) |
| A61B 50/30 | (2016.01) |
| A61B 17/68 | (2006.01) |
| A61B 90/00 | (2016.01) |
| A61B 17/84 | (2006.01) |
| A61B 50/20 | (2016.01) |

(52) U.S. Cl.
CPC ........ *A61B 17/8872* (2013.01); *A61B 17/686* (2013.01); *A61B 17/8861* (2013.01); *A61B 50/30* (2016.02); *A61B 17/842* (2013.01); *A61B 17/8863* (2013.01); *A61B 50/20* (2016.02); *A61B 2090/061* (2016.02)

(58) Field of Classification Search
CPC .......................... A61B 17/8872; A61B 17/686
See application file for complete search history.

(56) References Cited

U.S. PATENT DOCUMENTS

| | | | |
|---|---|---|---|
| 517,668 | A | 4/1894 | Still |
| 1,486,527 | A | 3/1924 | Larkin |
| 1,516,652 | A | 11/1924 | Tomkinson |
| 2,148,164 | A | 2/1939 | Krippendorf |
| 2,326,453 | A | 8/1943 | Gelpcke |

(Continued)

FOREIGN PATENT DOCUMENTS

| | | |
|---|---|---|
| CN | 201046258 Y | 4/2008 |
| EP | 1614402 A1 | 1/2006 |

(Continued)

OTHER PUBLICATIONS

International Search Report in International Appliction No. PCT/US15/50483, dated Dec. 28, 2015.

(Continued)

*Primary Examiner* — Andrew Yang
(74) *Attorney, Agent, or Firm* — Venable LLP; Michele V. Frank

(57) ABSTRACT

A kit for implanting a woven retention device into bone includes a woven retention device, a delivery tube, and a push rod. The woven retention device includes a distal end that is tapered to a distal tip, a proximal end for receiving a fastener, and a sleeve body between the distal and proximal ends. The delivery tube includes distal and proximal openings, and a compression portion over at least a distal end of the delivery tube. The push rod can be slideably received within the delivery tube and has a distal end for pushing the woven retention device through the distal opening of the delivery tube.

24 Claims, 18 Drawing Sheets

(56) References Cited

U.S. PATENT DOCUMENTS

| | | |
|---|---|---|
| 2,388,693 A | 11/1945 | Jeckel |
| 2,879,687 A | 3/1959 | Leimbach |
| 2,936,670 A | 5/1960 | Walter |
| 2,983,182 A | 5/1961 | Shobert |
| 3,054,406 A | 9/1962 | Francis |
| 3,187,752 A | 6/1965 | Glick |
| 3,199,398 A | 8/1965 | Weisz |
| 3,232,163 A | 2/1966 | George |
| 3,363,502 A | 1/1968 | Florentine |
| 3,371,573 A | 3/1968 | Koreki |
| 3,710,789 A | 1/1973 | Ersek |
| 3,714,862 A | 2/1973 | Berger |
| 3,921,496 A | 11/1975 | Helderman |
| 4,011,602 A | 3/1977 | Rybicki et al. |
| 4,064,567 A | 12/1977 | Burstein et al. |
| 4,158,984 A | 6/1979 | Griffiths |
| 4,182,339 A | 1/1980 | Hardy, Jr. |
| 4,205,399 A | 6/1980 | Shalaby et al. |
| 4,304,169 A | 12/1981 | Cimprich et al. |
| 4,383,527 A | 5/1983 | Asnis et al. |
| 4,394,370 A | 7/1983 | Jefferies |
| 4,409,974 A | 10/1983 | Freedland |
| 4,453,539 A | 6/1984 | Raftopoulos et al. |
| 4,520,821 A | 6/1985 | Schmidt et al. |
| 4,563,489 A | 1/1986 | Urist |
| 4,566,466 A | 1/1986 | Ripple et al. |
| 4,567,917 A | 2/1986 | Millard |
| 4,584,722 A | 4/1986 | Levy et al. |
| 4,610,688 A | 9/1986 | Silvestrini et al. |
| 4,640,271 A | 2/1987 | Lower |
| 4,708,132 A | 11/1987 | Silvestrini |
| 4,716,807 A | 1/1988 | Fischer |
| 4,753,149 A | 6/1988 | Celani |
| 4,760,843 A | 8/1988 | Fischer et al. |
| 4,777,860 A | 10/1988 | Bassett et al. |
| 4,790,852 A | 12/1988 | Noiles |
| 4,803,909 A | 2/1989 | Smith |
| 4,870,957 A | 10/1989 | Goble et al. |
| 4,894,063 A | 1/1990 | Nashef |
| 4,913,028 A | 4/1990 | Yoshiya |
| 4,917,700 A | 4/1990 | Aikins |
| 5,013,318 A | 5/1991 | Spranza, III |
| 5,059,211 A | 10/1991 | Stack et al. |
| 5,084,050 A | 1/1992 | Draenert |
| 5,171,148 A | 12/1992 | Wasserman et al. |
| 5,186,992 A | 2/1993 | Kite, III |
| 5,211,647 A | 5/1993 | Schmieding |
| 5,221,261 A | 6/1993 | Termin et al. |
| 5,257,571 A | 11/1993 | Richardson |
| 5,268,001 A | 12/1993 | Nicholson et al. |
| 5,300,075 A | 4/1994 | Gordon |
| 5,354,292 A | 10/1994 | Braeuer et al. |
| 5,380,334 A | 1/1995 | Torrie et al. |
| 5,383,387 A | 1/1995 | Chesterfield et al. |
| 5,385,077 A | 1/1995 | Akiyama et al. |
| 5,443,499 A | 8/1995 | Schmitt |
| 5,456,721 A | 10/1995 | Legrand |
| 5,458,601 A | 10/1995 | Young, Jr. et al. |
| 5,501,133 A | 3/1996 | Brookstein et al. |
| 5,520,084 A | 5/1996 | Chesterfield et al. |
| 5,571,184 A | 11/1996 | DeSatnick |
| 5,628,788 A | 5/1997 | Pinchuk |
| 5,629,077 A | 5/1997 | Turnlund et al. |
| 5,641,256 A | 6/1997 | Gundy |
| 5,713,904 A | 2/1998 | Errico et al. |
| 5,716,359 A | 2/1998 | Ojima et al. |
| 5,718,159 A | 2/1998 | Thompson |
| 5,725,541 A | 3/1998 | Anspach, III et al. |
| 5,741,325 A | 4/1998 | Chaikof et al. |
| 5,756,457 A | 5/1998 | Wang et al. |
| 5,758,562 A | 6/1998 | Thompson |
| 5,766,250 A | 6/1998 | Chervitz et al. |
| 5,785,713 A | 7/1998 | Jobe |
| D397,794 S | 9/1998 | Geber |
| 5,849,013 A | 12/1998 | Whittaker et al. |
| 5,871,504 A | 2/1999 | Eaton et al. |
| 5,876,432 A | 3/1999 | Lau et al. |
| 5,904,685 A | 5/1999 | Walawalkar |
| 5,941,901 A | 8/1999 | Egan |
| 5,957,974 A | 9/1999 | Thompson et al. |
| 5,961,524 A | 10/1999 | Crombie |
| 5,984,926 A | 11/1999 | Jones |
| 6,019,786 A | 2/2000 | Thompson |
| 6,039,740 A | 3/2000 | Olerud |
| 6,042,592 A | 3/2000 | Schmitt |
| 6,056,751 A | 5/2000 | Fenton, Jr. |
| 6,080,155 A | 6/2000 | Michelson |
| 6,099,530 A | 8/2000 | Simonian et al. |
| 6,126,663 A | 10/2000 | Hair |
| 6,143,029 A | 11/2000 | Rippstein |
| 6,231,606 B1 | 5/2001 | Graf et al. |
| 6,241,757 B1 | 6/2001 | An et al. |
| 6,264,676 B1 | 7/2001 | Gellman et al. |
| 6,314,856 B1 | 11/2001 | Keith et al. |
| 6,319,255 B1 | 11/2001 | Grundei et al. |
| 6,325,822 B1 | 12/2001 | Chouinard et al. |
| 6,336,940 B1 | 1/2002 | Graf et al. |
| 6,342,068 B1 | 1/2002 | Thompson |
| 6,355,044 B1 | 3/2002 | Hair |
| 6,375,662 B1 | 4/2002 | Schmitt |
| 6,398,807 B1 | 6/2002 | Chouinard et al. |
| 6,413,260 B1 | 7/2002 | Berrevoets et al. |
| 6,495,227 B1 | 12/2002 | Cahuzac |
| 6,500,203 B1 | 12/2002 | Thompson et al. |
| 6,540,770 B1 | 4/2003 | Tornier et al. |
| 6,544,281 B2 | 4/2003 | ElAttrache et al. |
| 6,551,352 B2 | 4/2003 | Clerc et al. |
| 6,582,461 B1 | 6/2003 | Burmeister et al. |
| 6,616,694 B1 | 9/2003 | Hart |
| 6,616,996 B1 | 9/2003 | Keith et al. |
| 6,622,604 B1 | 9/2003 | Chouinard et al. |
| 6,631,666 B2 | 10/2003 | Cahuzac |
| 6,645,211 B2 | 11/2003 | Magana |
| 6,652,571 B1 | 11/2003 | White et al. |
| 6,669,706 B2 | 12/2003 | Schmitt et al. |
| 6,685,738 B2 | 2/2004 | Chouinard et al. |
| 6,746,483 B1 | 6/2004 | Bojarski et al. |
| 6,767,350 B1 | 7/2004 | Lob |
| 6,792,979 B2 | 9/2004 | Konya et al. |
| 6,827,743 B2 | 12/2004 | Eisermann et al. |
| 6,840,769 B2 | 1/2005 | Augthun et al. |
| D503,802 S | 4/2005 | Bjarnason |
| 6,875,216 B2 | 4/2005 | Wolf |
| 6,908,466 B1 | 6/2005 | Bonutti et al. |
| 6,942,666 B2 | 9/2005 | Overaker et al. |
| 6,942,693 B2 | 9/2005 | Chouinard et al. |
| 6,991,647 B2 | 1/2006 | Jadhav |
| 7,004,967 B2 | 2/2006 | Chouinard et al. |
| 7,022,124 B2 | 4/2006 | Takei et al. |
| 7,052,513 B2 | 5/2006 | Thompson |
| 7,093,527 B2 | 8/2006 | Rapaport et al. |
| 7,101,183 B2 | 9/2006 | Augthun et al. |
| 7,213,495 B2 | 5/2007 | McCullagh et al. |
| 7,237,466 B2 | 7/2007 | Chen |
| 7,255,712 B1 | 8/2007 | Steinberg |
| 7,275,471 B2 | 10/2007 | Nishri et al. |
| 7,279,008 B2 | 10/2007 | Brown et al. |
| 7,309,355 B2 | 12/2007 | Donnelly et al. |
| 7,311,031 B2 | 12/2007 | McCullagh et al. |
| 7,341,592 B1 | 3/2008 | Walters et al. |
| 7,341,601 B2 | 3/2008 | Eisermann et al. |
| 7,344,559 B2 | 3/2008 | Gray et al. |
| 7,407,512 B2 | 8/2008 | Bojarski et al. |
| 7,435,254 B2 | 10/2008 | Chouinard et al. |
| 7,513,865 B2 | 4/2009 | Bourne et al. |
| 7,547,321 B2 | 6/2009 | Silvestri et al. |
| 7,572,283 B2 | 8/2009 | Meridew |
| 7,572,298 B2 | 8/2009 | Roller et al. |
| 7,582,108 B2 | 9/2009 | Hierlemann et al. |
| D612,499 S | 3/2010 | Ondracek et al. |
| 7,682,392 B2 | 3/2010 | Serhan et al. |
| 7,699,893 B2 | 4/2010 | Donnelly et al. |
| 7,731,750 B2 | 6/2010 | Bojarski et al. |
| 7,749,233 B2 | 7/2010 | Farr et al. |

(56) References Cited

U.S. PATENT DOCUMENTS

| | | | |
|---|---|---|---|
| 7,758,642 B2 | 7/2010 | Bojarski et al. |
| 7,785,357 B2 | 8/2010 | Guan et al. |
| D626,648 S | 11/2010 | Ahlgren |
| 7,824,433 B2 | 11/2010 | Williams |
| 7,833,249 B2 | 11/2010 | Shaolian et al. |
| 7,892,203 B2 | 2/2011 | Lenker et al. |
| 7,896,901 B2 | 3/2011 | Whittaker |
| 7,938,853 B2 | 5/2011 | Chouinard et al. |
| 7,963,972 B2 | 6/2011 | Foerster et al. |
| 7,967,851 B2 | 6/2011 | Bickley et al. |
| 7,988,732 B2 | 8/2011 | Bojarski et al. |
| 8,052,720 B2 | 11/2011 | Kuester et al. |
| 8,114,141 B2 | 2/2012 | Appenzeller et al. |
| 8,128,626 B2 | 3/2012 | Justin |
| 8,142,415 B2 | 3/2012 | Warnock, Jr. et al. |
| 8,151,682 B2 | 4/2012 | Lilburn et al. |
| 8,162,998 B2 | 4/2012 | Schlienger et al. |
| 8,163,031 B2 | 4/2012 | Truckai et al. |
| 8,202,306 B2 | 6/2012 | Dreyfuss |
| 8,221,479 B2 | 7/2012 | Glazer et al. |
| 8,226,714 B2 | 7/2012 | Beck, Jr. et al. |
| 8,226,715 B2 | 7/2012 | Hwang et al. |
| 8,241,340 B2 | 8/2012 | Froehlich |
| 8,257,395 B2 | 9/2012 | Bhatnagar et al. |
| 8,298,262 B2 | 10/2012 | Stone et al. |
| 8,308,779 B2 | 11/2012 | Reiley |
| 8,317,799 B2 | 11/2012 | Schon et al. |
| 8,317,863 B2 | 11/2012 | Cauldwell et al. |
| 8,347,772 B2 | 1/2013 | Dow et al. |
| 8,353,941 B2 | 1/2013 | Fricker et al. |
| 8,361,078 B2 | 1/2013 | Beyar et al. |
| 8,366,711 B2 | 2/2013 | Rabiner et al. |
| 8,372,115 B2 | 2/2013 | Kohm et al. |
| 8,382,849 B2 | 2/2013 | Thomas |
| 8,414,635 B2 | 4/2013 | Hyodoh et al. |
| 8,420,113 B2 | 4/2013 | Zhao |
| 8,435,293 B2 | 5/2013 | Donnelly et al. |
| 8,443,706 B2 | 5/2013 | Egres, Jr. |
| 8,459,164 B2 | 6/2013 | Lilburn et al. |
| 8,523,902 B2 | 9/2013 | Heaven et al. |
| 8,523,916 B2 | 9/2013 | Anderson et al. |
| 8,523,951 B2 | 9/2013 | Kania |
| 8,545,499 B2 | 10/2013 | Lozier et al. |
| 8,546,456 B2 | 10/2013 | Rose et al. |
| 8,546,752 B2 | 10/2013 | Henion et al. |
| 8,568,413 B2 | 10/2013 | Mazur et al. |
| 8,585,762 B2 | 11/2013 | Hall |
| 8,591,582 B2 | 11/2013 | Anderson et al. |
| 8,617,185 B2 | 12/2013 | Bonutti et al. |
| 8,636,753 B2 | 1/2014 | Buevich et al. |
| 8,652,171 B2 | 2/2014 | Stone et al. |
| 8,663,296 B2 | 3/2014 | Williams |
| 8,663,672 B2 | 3/2014 | Manrique et al. |
| 8,671,815 B2 | 3/2014 | Hancock et al. |
| 8,677,874 B2 | 3/2014 | Lilburn et al. |
| 8,690,962 B2 | 4/2014 | Dignam et al. |
| 8,696,748 B2 | 4/2014 | Bojarski et al. |
| 8,709,055 B2 | 4/2014 | Beyar et al. |
| 8,721,519 B2 | 5/2014 | Sheu et al. |
| 8,747,470 B2 | 6/2014 | Beck, Jr. et al. |
| 8,753,391 B2 | 6/2014 | Lu et al. |
| 8,770,081 B2 | 7/2014 | David et al. |
| 8,794,118 B2 | 8/2014 | Dow et al. |
| 8,833,224 B2 | 9/2014 | Thompson et al. |
| 8,857,304 B2 | 10/2014 | Govari et al. |
| 8,910,554 B2 | 12/2014 | Kinugasa |
| D723,166 S | 2/2015 | Igaki et al. |
| 8,956,394 B1 | 2/2015 | McDonnell |
| 8,992,537 B1 | 3/2015 | McDonnell |
| 9,388,517 B2 | 7/2016 | Lilburn et al. |
| 9,416,472 B2 | 8/2016 | Scherrible et al. |
| 9,532,806 B2 | 1/2017 | McDonnell |
| 9,585,695 B2 | 3/2017 | Jones et al. |
| 2002/0055749 A1 | 5/2002 | Esnouf et al. |
| 2002/0083821 A1 | 7/2002 | Uchida |
| 2002/0143340 A1 | 10/2002 | Kaneko |
| 2002/0147454 A1 | 10/2002 | Neto |
| 2003/0036761 A1 | 2/2003 | Smothers et al. |
| 2003/0045880 A1 | 3/2003 | Michelson |
| 2004/0024456 A1 | 2/2004 | Brown, Jr. et al. |
| 2004/0068267 A1 | 4/2004 | Harvie et al. |
| 2004/0094024 A1 | 5/2004 | Kim |
| 2004/0133204 A1 | 7/2004 | Davies |
| 2005/0015154 A1 | 1/2005 | Lindsey et al. |
| 2005/0070930 A1 | 3/2005 | Kammerer |
| 2005/0150370 A1 | 7/2005 | Nishri et al. |
| 2005/0216006 A1 | 9/2005 | Orbay et al. |
| 2005/0251143 A1 | 11/2005 | Dillard |
| 2005/0255230 A1 | 11/2005 | Clerc et al. |
| 2006/0089646 A1 | 4/2006 | Bonutti |
| 2006/0129148 A1 | 6/2006 | Simmons et al. |
| 2007/0060923 A1 | 3/2007 | Dreyfuss |
| 2007/0093899 A1 | 4/2007 | Dutoit et al. |
| 2007/0118131 A1 | 5/2007 | Gooch |
| 2007/0118144 A1 | 5/2007 | Truckai et al. |
| 2007/0191956 A1 | 8/2007 | Prewett et al. |
| 2007/0250114 A1 | 10/2007 | Drapeau |
| 2007/0270941 A1 | 11/2007 | Headley et al. |
| 2008/0027445 A1 | 1/2008 | Brown et al. |
| 2008/0255560 A1 | 10/2008 | Myers et al. |
| 2008/0262630 A1 | 10/2008 | Fulmer et al. |
| 2008/0281430 A1 | 11/2008 | Kelman et al. |
| 2009/0024147 A1 | 1/2009 | Ralph et al. |
| 2009/0136898 A1 | 5/2009 | Kim |
| 2009/0193961 A1 | 8/2009 | Jensen et al. |
| 2009/0216338 A1 | 8/2009 | Gingras et al. |
| 2009/0254124 A1 | 10/2009 | Bickley et al. |
| 2009/0279980 A1 | 11/2009 | Gruber |
| 2009/0306777 A1 | 12/2009 | Widmer et al. |
| 2010/0016940 A1 | 1/2010 | Shokoohi et al. |
| 2010/0076503 A1 | 3/2010 | Beyar et al. |
| 2010/0125273 A1 | 5/2010 | Schwieger et al. |
| 2010/0152786 A1 | 6/2010 | Behrbalk |
| 2010/0168505 A1 | 7/2010 | Inman et al. |
| 2010/0179591 A1 | 7/2010 | Saltzman et al. |
| 2010/0292738 A1 | 11/2010 | Reiley |
| 2010/0318085 A1 | 12/2010 | Austin et al. |
| 2010/0324607 A1 | 12/2010 | Davis |
| 2010/0331881 A1 | 12/2010 | Hart |
| 2011/0061519 A1 | 3/2011 | Fields |
| 2011/0106177 A1 | 5/2011 | Lewis |
| 2011/0144766 A1 | 6/2011 | Kale et al. |
| 2011/0184472 A1 | 7/2011 | Niederberger et al. |
| 2011/0213467 A1 | 9/2011 | Lozier et al. |
| 2011/0230948 A1 | 9/2011 | Ehrenreich et al. |
| 2012/0065649 A1 | 3/2012 | Towler |
| 2012/0123416 A1 | 5/2012 | Gelfand et al. |
| 2012/0172934 A1 | 7/2012 | Fisher et al. |
| 2012/0239145 A1 | 9/2012 | Peterson et al. |
| 2012/0245704 A1 | 9/2012 | Childs |
| 2012/0259372 A1 | 10/2012 | Glazer et al. |
| 2012/0264084 A1 | 10/2012 | Hansson et al. |
| 2013/0013065 A1 | 1/2013 | Bills |
| 2013/0014544 A1 | 1/2013 | Winkler |
| 2013/0018318 A1 | 1/2013 | Ravichandran et al. |
| 2013/0103166 A1 | 4/2013 | Butler et al. |
| 2013/0131684 A1 | 5/2013 | Farrell |
| 2013/0178946 A1 | 7/2013 | Monaghan et al. |
| 2013/0184819 A1 | 7/2013 | Donnelly et al. |
| 2013/0226204 A1 | 8/2013 | Kumar |
| 2013/0289621 A1 | 10/2013 | Fulmer et al. |
| 2014/0046454 A1 | 2/2014 | Rose et al. |
| 2014/0052178 A1 | 2/2014 | Dooney, Jr. |
| 2014/0090549 A1 | 4/2014 | Hurlen |
| 2014/0094805 A1 | 4/2014 | Bonutti et al. |
| 2014/0100590 A1 | 4/2014 | Gingras et al. |
| 2014/0128916 A1 | 5/2014 | Williams |
| 2014/0207145 A1 | 7/2014 | Sennett |
| 2014/0277150 A1 | 9/2014 | Jones et al. |
| 2014/0277449 A1 | 9/2014 | Jones |
| 2014/0358145 A1 | 12/2014 | Schaller et al. |
| 2015/0045831 A1 | 2/2015 | Allen |
| 2015/0275408 A1 | 10/2015 | Tahara et al. |
| 2015/0342764 A1 | 12/2015 | Ramzipoor et al. |

(56) References Cited

U.S. PATENT DOCUMENTS

| | | |
|---|---|---|
| 2016/0010248 A1 | 1/2016 | Lariviere et al. |
| 2016/0038187 A1 | 2/2016 | McDonnell |
| 2016/0038206 A1 | 2/2016 | McDonnell |
| 2016/0058524 A1 | 3/2016 | Tehrani et al. |
| 2016/0074071 A1 | 3/2016 | McDonnell et al. |
| 2016/0074072 A1 | 3/2016 | McDonnell et al. |
| 2016/0074084 A1 | 3/2016 | McDonnell et al. |
| 2016/0168769 A1 | 6/2016 | McDonnell |
| 2016/0183942 A1 | 6/2016 | Allen |
| 2016/0317332 A1 | 11/2016 | Lilburn et al. |
| 2016/0345676 A1 | 12/2016 | Bruce et al. |
| 2017/0035481 A1 | 2/2017 | Magee et al. |
| 2017/0035482 A1 | 2/2017 | Magee et al. |
| 2017/0071634 A1 | 3/2017 | McDonnell |
| 2017/0128100 A1 | 5/2017 | Jones et al. |
| 2017/0165077 A1 | 6/2017 | McDonnell |
| 2017/0215934 A1 | 8/2017 | McDonnell |

FOREIGN PATENT DOCUMENTS

| | | |
|---|---|---|
| FR | 2725615 A1 | 4/1996 |
| FR | 2955259 A1 | 7/2011 |
| GB | 2 307 179 A | 5/1997 |
| WO | 1983/002555 A1 | 8/1983 |
| WO | 1989/001320 A1 | 2/1989 |
| WO | 1994/007425 A1 | 4/1994 |
| WO | 1996/003084 A1 | 2/1996 |
| WO | 2001/056506 A1 | 8/2001 |
| WO | 2001/070135 A2 | 9/2001 |
| WO | 2006/105935 A1 | 10/2006 |
| WO | 2007/103404 A2 | 9/2007 |
| WO | WO-2010/042293 A1 | 4/2010 |
| WO | 2012/116319 A2 | 8/2012 |
| WO | 2012/121726 A1 | 9/2012 |
| WO | 2013/004763 A1 | 1/2013 |
| WO | 2016/022491 A1 | 2/2016 |
| WO | 2016/044471 A1 | 3/2016 |
| WO | 2017/024277 A1 | 2/2017 |
| WO | 2017/024280 A1 | 2/2017 |

OTHER PUBLICATIONS

International Search Report and Written Opinion in related International Application No. PCT/US2015/050506, dated Dec. 14, 2015.
International Search Report and Written Opinion in corresponding International Application No. PCT/US2015/065028, dated Feb. 12, 2016.
McDonnell et al., U.S. Appl. No. 14/569,541, filed Dec. 12, 2014.
ACE Surgical Supply Co., Inc. Titanium Augmentation Micro Mesh—7, http://www.acesurgical.com/bone-grafting/graft-holding-mesh-foils/mic . . . .
Biomesh® Neurological Patches N3L—Spinal dura-mater substitutes—Cousin Biotech, <http://www.cousin-biotech.com/uk/produit.php?idrubrique=16&idspecialite=35&idproduit=81>.
Bioretec—ActivaScrew Cannulated—Surgical Technique, <http://www.bioretec.com/products/pro_orthotrauma/activascrew-cannulated/surgical-technique.php>.
ConMed, Fixation Implants, <http://www.conmed.com/products/knee-fixation.php>.
GORE-TEX® Soft Tissue Patch, <http://www.goremedical.com/stp/>.
Medtronic Sofamor Danek, Vertex® Max, Reconstruction System Surgical Technique, © 2005.
The Open Prosthetics Project: suspension, <http://openprosthetics.org/suspension>.
Synthes GmbH, Angular Stable Locking System (ASLS). For angular stable locking of intra-medullary nails, Technique Guide, © Oct. 2008.
Synthes GmbH, DLS Dynamic Locking Screw. Combined with LCP Locking Compression Plate, Instructions for Use, © Oct. 2012.
Vicryl® (polyglactin 910) Woven Mesh—Ethicon, <http://www.ethicon.com/healthcare-professionals/products/tissue-hemia/mesh/vicryl-polyglactin-910-woven-mesh>.
K.P. Chellamani et al., Medical textiles using Braiding Technology, Journal of Academia and Industrial Research (JAIR), vol. 2, Issue 1, Jun. 2013, pp. 21-26.
Ho Jung Kang et al., An Experimental Intraarticular Implantation of Woven Carbon Fiber Pad into Osteochondral Defect of the Femoral Condyle in Rabbit, Yonsei Medical Journal, vol. 32, No. 2, 1991, pp. 108-116.
D. S. Muckle et al., Biological Response to Woven Carbon Fibre Pads in the Knee, The Journal of Bone and Joint Surgery, 1989, 7I-B, pp. 60-62.
Takanobu Nishizuka et al., Intramedullary-fixation Technique for Long Bone Fragility Fractures Using Bioabsorbable Materials, Orthopedic Research Annual Meeting, Mar. 2014.
Maureen Suchenski, M.D. et al., Material Properties and Composition of Soft-Tissue Fixation, Arthroscopy: The Journal of Arthroscopic and Related Surgery, vol. 26, No. 6, Jun. 2010, pp. 821-831.
Stephanie C. Von Plocki, et al., Biodegradable Sleeves for Metal Implants to Prevent Implant-Associated Infection: An Experimental In Vivo Study in Sheep, Veterinary Surgery, vol. 41, Issue 3, Apr. 2012, pp. 410-421.
Andre Weimann, M.D., et al., Primary Stability of Bone-Patellar Tendon-Bone Graft Fixation With Biodegradable Pins, Arthroscopy: The Journal of Arthroscopic and Related Surgery, vol. 19, No. 10, Dec. 2003, pp. 1097-1102.
International Search Report and Written Opinion in International Application No. PCT/US2015/043471, dated Nov. 3, 2015.
International Search Report and Written Opinion in International Application No. PCT/US2016/045899, dated Oct. 11, 2016.
International Search Report and Written Opinion in International Application No. PCT/US2016/045903, dated Nov. 2, 2016.
U.S. Appl. No. 29/524,091: Office Action dated Jun. 5, 2015.
U.S. Appl. No. 29/524,091: Notice of Allowance dated Jan. 25, 2016.
U.S. Appl. No. 29/524,091, filed Apr. 16, 2015.
Alves et al., "Injectability Evaluation of Tricalcium Phosphate Bone Cement", J Mater Sci Mater Med., vol. 19(5), 2008 (Abstract).
Non-Final Office Action issued in corresponding U.S. Appl. No. 14/209,514 dated Jul. 27, 2017 (10 pages).
Non-Final Office Action issued in corresponding U.S. Appl. No. 14/569,541 dated Feb. 27, 2017 (21 pages).
Non-Final Office Action issued in corresponding U.S. Appl. No. 14/487,895 dated Mar. 24, 2017 (6 pages).
Non-Final Office Action issued in corresponding U.S. Appl. No. 15/359,021 dated Feb. 1, 2017 (16 pages).
Notice of Allowance issued in corresponding U.S. Appl. No. 15/359,021 dated Sep. 13, 2017 (8 pages).

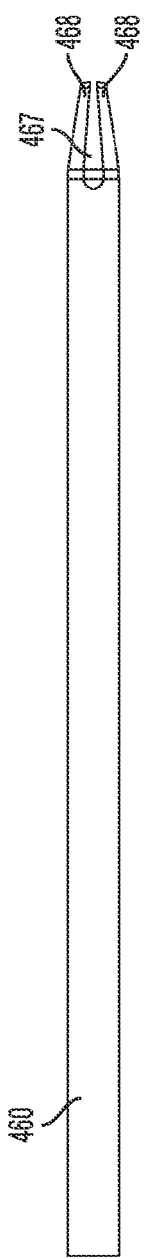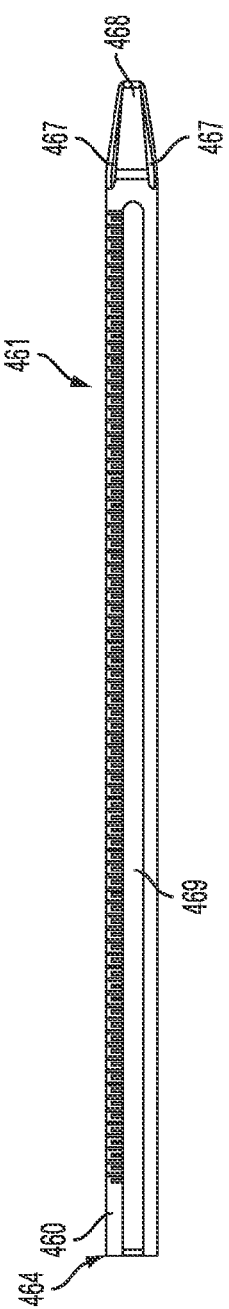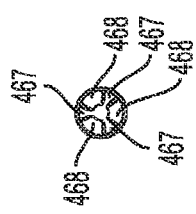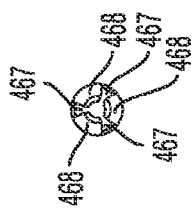

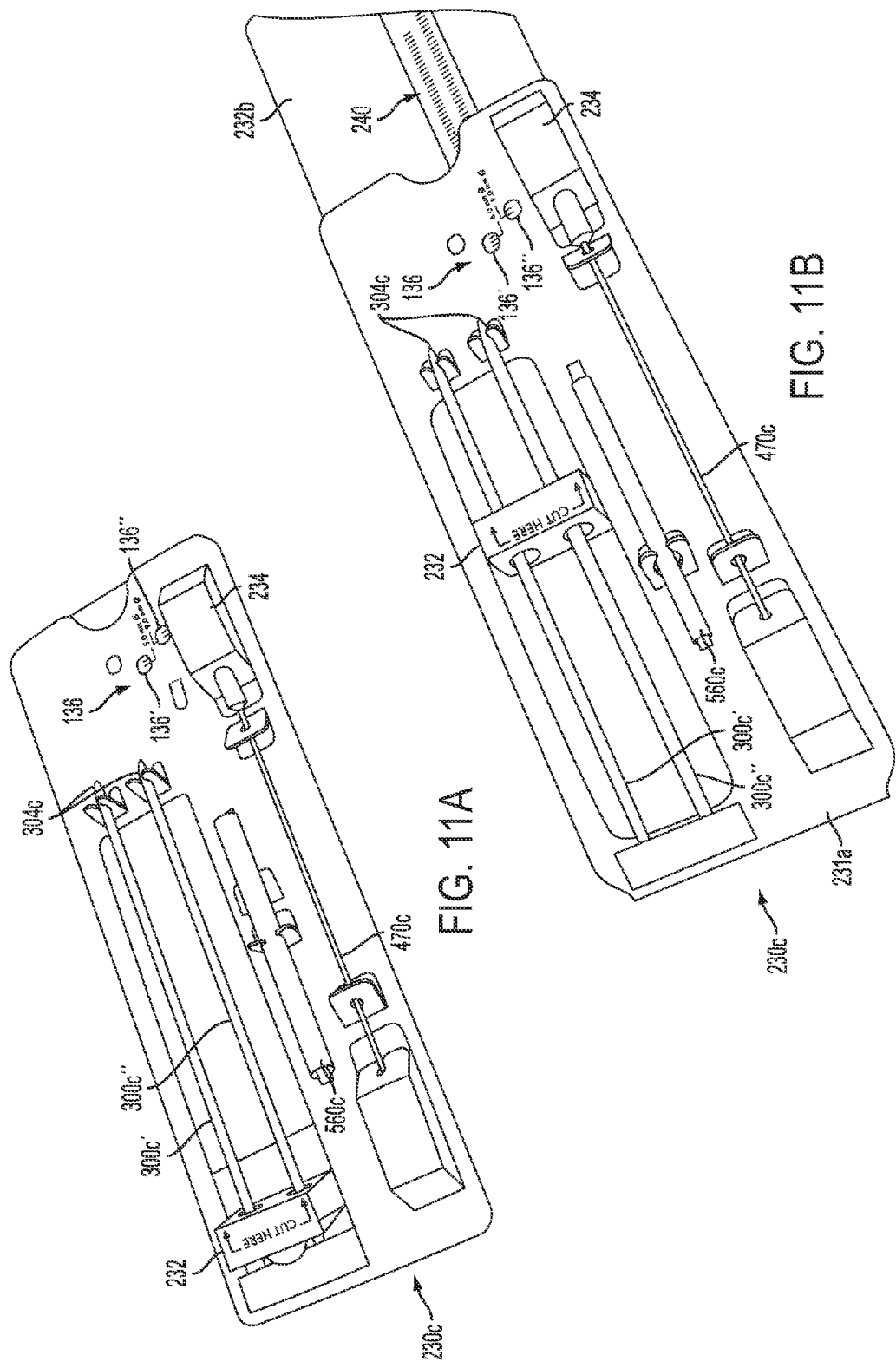

WOVEN RETENTION DEVICES, SYSTEMS, PACKAGING, AND RELATED METHODS

TECHNICAL FIELD OF INVENTION

The present invention relates generally to a woven retention device kit and method for inserting a woven retention device into bone.

BACKGROUND

In orthopedic surgery it is common to secure a bone screw to a patient's bone. Bone fracture repair is surgery to fix a broken bone using plates, nails, screws, or pins. It is common in the treatment of fractures to attach a plate to the bone utilizing bone screws. The resulting construct prevents motion of the fractured bone so that the bone can heal. Alternatively, one or more screws may be inserted across the break to hold it place.

In the treatment of spinal disorders, pedicle screws are inserted into the patient's vertebrae to serve as anchor points that can then be connected with a rod. This construct prevents motion of the vertebral segments that are to be fused.

In the treatment of detached tendons, screw-like tissue anchors are inserted into the patient's bone to serve as an anchor for the reattachment of the tendon.

One complication with the use of bone screws is the loss of fixation or grip between the bone screw and the patient's bone. Another complication with the use of bone screws is the stripping of the hole in the bone when the bone screw is inserted. This results in the loss of purchase and holding strength of the bone screw.

The presence of osteoporotic bone can increase the likelihood of complications by reducing the purchase or grip of the bone screw to the patient's bone, resulting in a loss of holding strength and loosening of the bone screw or pullout of the bone screw.

Current solutions to secure bone screws have not adequately addressed screw failure and the underlying causes of screw failure. In addition, there exists a need for simple and effective methods to insert such orthopedic devices and systems, as well as simple and easy to use kits that can enable surgeons to more effective treat patients.

BRIEF SUMMARY OF THE INVENTION

According to an embodiment of the present invention, a kit for implanting a woven retention device into bone is provided. The kit may include a woven retention device having a distal end that is tapered to a distal tip, a proximal end for receiving a fastener, and a sleeve body between the distal and proximal ends. The kit may also include a delivery tube including a distal opening and a proximal opening, the delivery tube having a compression portion over at least a distal end of the delivery tube. The kit also may include a push rod to be slideably received within the delivery tube and having a distal end to push the woven retention device through the distal opening of the delivery tube.

According to some embodiments of the present invention, the woven retention device may be able to be radially compressed to a compressed state when at least part of the sleeve body is within the compression portion. The sleeve body may have a first outer diameter in an uncompressed state and a second outer diameter in the compressed state, the second outer diameter being smaller than the first outer diameter. The compression portion can include a narrowed region at or near the distal opening of the delivery tube, the narrowed region having an inner diameter that is less than the first outer diameter of the sleeve body. The delivery tube may include a side wall opening extending longitudinally along at least a portion of the delivery tube. The push rod may be arranged such that at least a portion of the push rod extends outside of the delivery tube through the side wall opening during at least a portion of a progression of the distal end of the push rod inside the delivery tube. The compression portion may include a plurality of end slots in the delivery tube at a distal portion of the delivery tube. The plurality of slots can include an odd number of end slots at the distal portion of the delivery tube. The compression portion can further include a plurality of prongs disposed between slots of the plurality of slots, the prongs being able to compress the woven retention device as the woven retention device is advanced through the distal opening.

According to some embodiments of the present invention, the kit may further include a fastener that can be disposed within the woven retention device when the woven retention device is within the bone hole.

According to some embodiments of the present invention, the kit may further include a measuring device arranged to measure a desired length of the woven retention device to be inserted into the bone hole.

According to some embodiments of the present invention, the kit may further include a cutting device to cut the woven retention device based on the desired length measured by the measuring device. The measuring device may include indicia arranged to indicate a distance from the distal tip of the woven retention device to a reference point, the reference point being a point at which the woven retention device is able to be cut to achieve the desired length. The indicia can be arranged on a wall of the delivery tube. The designated cutting point may be the proximal opening of the delivery tube.

According to some embodiments of the present invention, the kit further includes a package containing at least one of the woven retention device, the delivery tube, and the push rod. The package may contain the woven retention device. The indicia can be arranged on the package. The woven retention device may be mounted on the package in a predetermined relationship relative to the indicia. The package can further include the delivery tube. The woven retention device may be pre-loaded within the delivery tube. The package can include a mounting surface to which the woven retention device is mounted, a measuring surface including at least one set of measuring indicia, the measuring surface being slidable relative to the mounting surface, and a cutting indicator fixed to the measuring surface, the cutting indicator being able to indicate a location on the woven retention device where cutting is to be performed. The measuring surface may be slidably received within an envelope including the mounting surface. The measuring surface includes at least one window through which the at least one set of measuring indicia are viewable, the at least one window being arranged to indicate a distance from the distal tip of the woven retention device to the location where the cutting indicator indicates the cut is to be performed. The at least one set of measuring indicia can include a plurality of sets of measuring indicia, each set of the plurality of sets of measuring indicia being calibrated based on a diameter of the woven retention device when the woven retention device is in a relaxed state.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 6A-6E show various views of a delivery tube with a measurement scale and a side wall opening on the delivery tube, according to an embodiment of the invention.

FIGS. 11A and 11B show packaging elements of the woven retention device kit with the packaging including a measuring mechanism, according to an embodiment of the invention.

DETAILED DESCRIPTION OF THE INVENTION

Figure 1A:
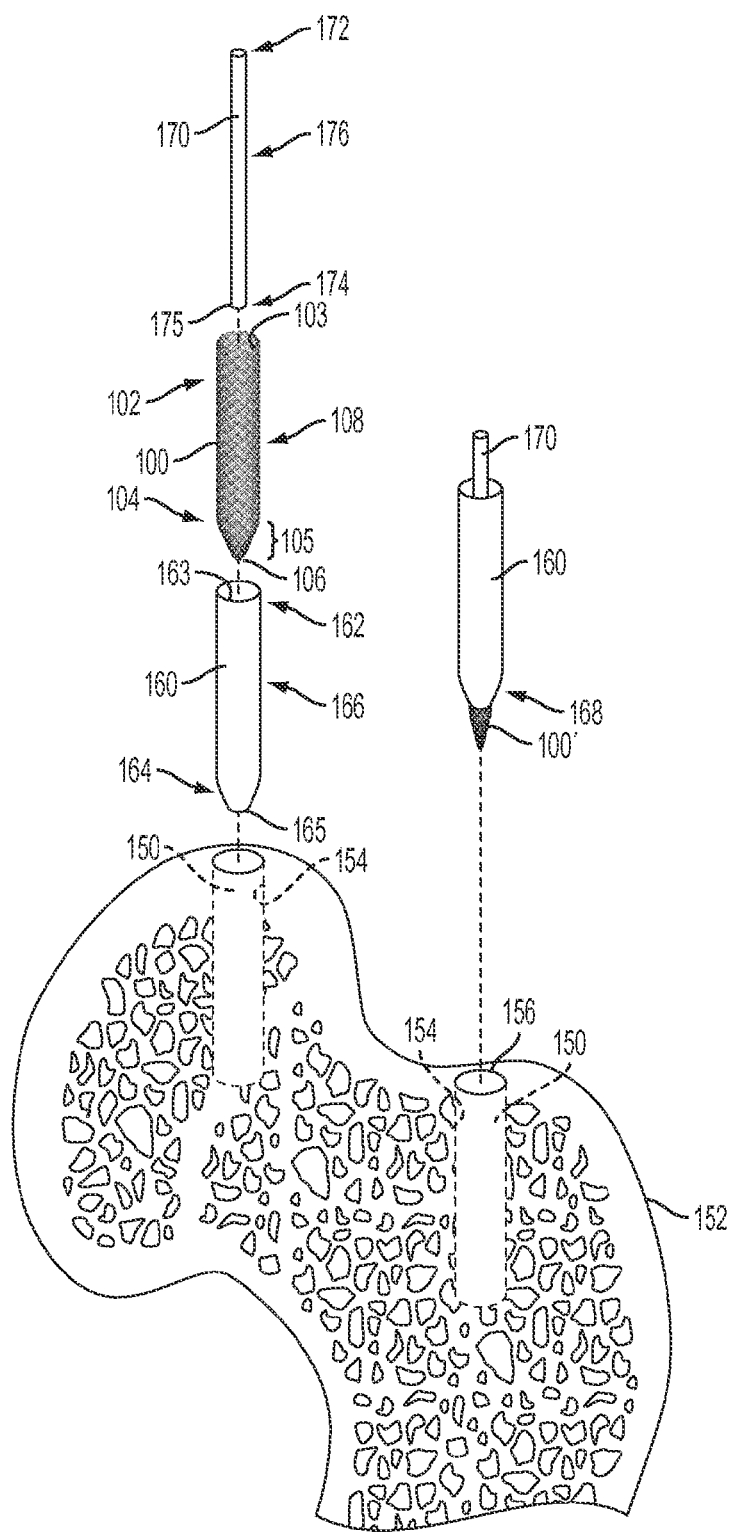
FIG. 1A shows an exploded view of a push rod, a woven retention device and a delivery tube that have not been pushed into each other, according to an embodiment of the invention, as well as the combination of the elements after the push rod has pushed the retention device through a portion of the delivery tube, according to an embodiment of the invention.

The devices, systems and methods described herein may be used in the area of orthopedics and, in particular, orthopedic repairs. These include various devices, systems and methods directed to fixing and/or retaining fasteners in orthopedic applications. Fixing or retaining fasteners to bone tissue is complicated by the underlining bone tissue. Understanding that an underlying cause of failure with internal fixation in bone tissue is the bone, the devices, systems and methods described herein provide for solutions that address the implant site. At the implant site, the hole and the bone benefit from an enhanced interface.

The fixation and/or retention devices, systems and methods described herein maximize fixation and/or retention in the bone tissue, including, osteoporotic bone, bone of a poor quality, and mechanically poor bone in addition to healthy bone tissue. The fixation and/or retention devices, systems and methods described herein may be used with any type of fixation including any types of screws, pins, or other fasteners.

The devices, systems and methods described herein enhance the interaction of a bone anchor to a bone hole to provide enhanced fixation. Additionally, the devices, systems and methods may repair the surface of the bone hole following damage to the bone hole as in the case of stripping of the hole in the bone when a bone screw is over-tightened. Also, the devices, systems and methods provide for an enhanced bone hole surface for the reattachment of tendons in, for example, anterior/posterior cruciate ligament repair procedures, rotator cuff repair procedures, etc. The devices enhance the surface of a bone hole to enhance fixation of a bone anchor to bone and permits bone ingrowth into its structure. The devices enhance the interaction between the surface of a bone hole and the fixation device. The devices interdigitate with the bony structure and interact with the fixation device. The device alone, as a single device, enhances the surface of a bone hole to enhance fixation of a bone anchor to bone and accommodates variations in the diameter and depth of the bone hole. The devices, systems and methods can enhance fixation without requiring the use of cement and/or adhesives. However, according to some embodiments, cements and/or adhesive can be used in addition to or in place of another bone anchor such as a screw, pin, or other orthopedic implant.

Also described herein are methods of using these devices and systems, including methods of inserting fixation devices into a bone hole of a patient. The methods may use insertion tools, kits, and/or device or system packaging that aid a user of the fixation devices to achieve a desired placement and fit of the fixation device within the bone hole of the patient, in order to achieve optimal performance of the fixation device. Also described herein are kits used for inserting fixation devices into a bone hole of a patient. The kits may include the fixation devices and tools for implanting the fixation devices. The kits may also include packaging of the fixation devices and tools.

Figure 1B:
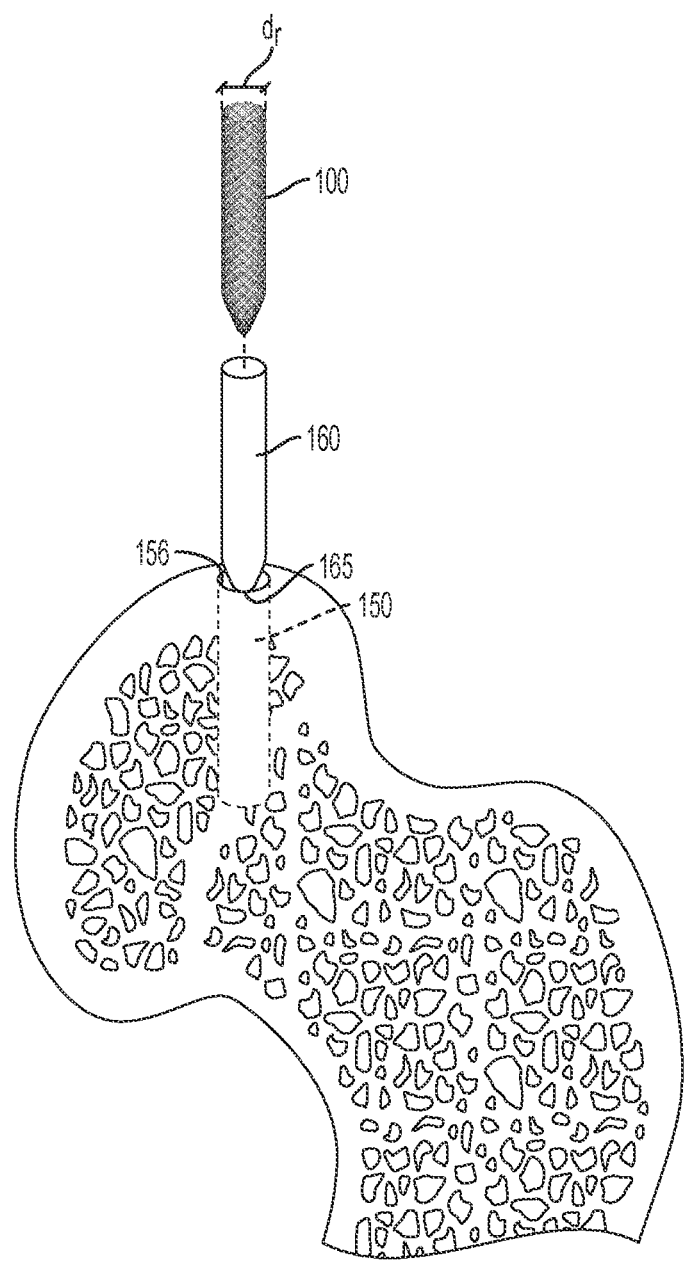
FIG. 1B shows a delivery tube that is positioned near a bone hole and a retention device configured to be pushed through the delivery tube, according to an embodiment of the invention.
Figure 1C:
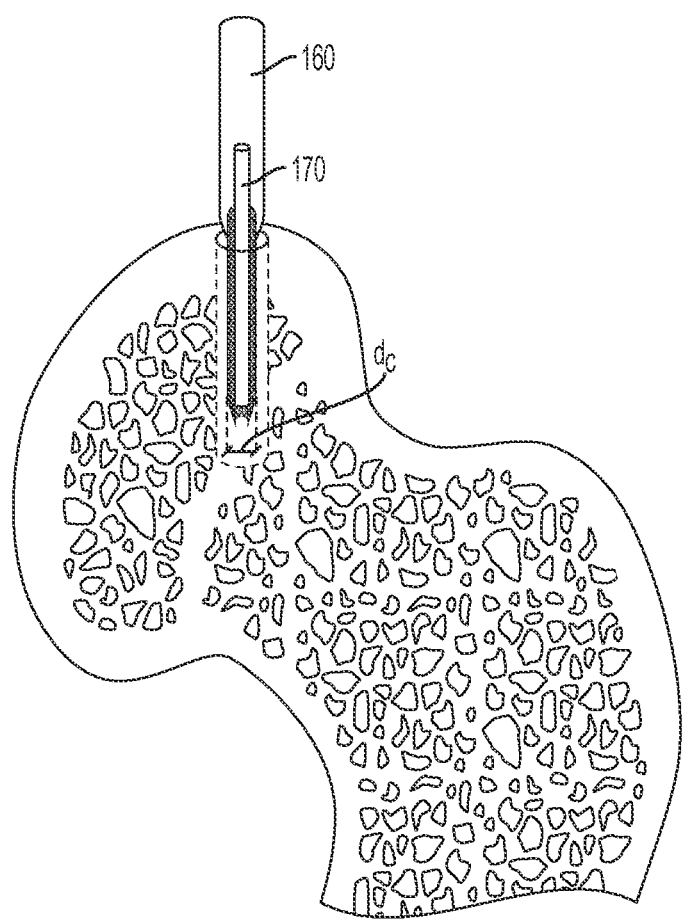
FIG. 1C shows a partial cut-away view of a delivery tube that is positioned near a bone hole and a push rod pushing the retention device through the delivery tube, according to an embodiment of the invention.

Referring now to the figures, FIGS. 1A, 1B, and 1C show examples of components of a kit including a woven retention device for inserting into a bone hole 150 of a bone 152 to interface with a bone surface 154 in the bone hole 150. FIG. 1A shows two woven retention devices 100, 100' for insertion into respective bone holes 150, 150'. Woven retention device 100 is shown in an exploded view with respect to a delivery tube 160 and push rod 170 used for inserting the woven retention device 100 into bone hole 150. The woven retention device 100 includes a proximal end 102 with a proximal opening 103, a distal end 104 that is tapered 105 to a distal tip 106, and a sleeve body 108 extending between the proximal and distal ends 102, 104. The proximal end 102 may be able to receive a fastener (not shown in FIG. 1A) through the proximal opening 103. The delivery tube 160 also includes a proximal end 162 with a proximal opening 163, a distal end 164 with a distal opening 165, and a tube body 166 extending between the proximal and distal ends 162, 164. The push rod 170 has a proximal end 172, a distal end 174 with a distal tip 175, and a rod body 176.

In an embodiment, a method of using a kit for inserting the woven retention device 100 into the bone hole 150 includes pushing the woven retention device 100 through the delivery tube 160 using the push rod 170. For example, FIG. 1A shows woven retention device 100' being pushed through the delivery tube 160 with the push rod 170. In the embodiment shown, at least part of the push rod 170 is inserted into the delivery tube 160 through the proximal opening 163 of the delivery tube 160, and the distal tip 175 of the push rod 170 exerts a force on an interior of the woven retention device 100' in at least the distal end 104 of the woven retention device 100'. It is contemplated that the tip 175 of the push rod 170 may push on a distal-most interior wall of the distal tip 106 and/or on at least a portion of the tapered portion 105.

In some embodiments, the distal tip of the push rod may be shaped to at least partially conform to a shape of the interior surface of the distal tip of the tapered portion of the woven retention device. For example, the distal tip of the push rod may be tapered or otherwise shaped to contact the inner surface of the woven retention device. In some embodiments, the distal tip of the woven retention devices may be closed, while in other embodiments the distal tip may have an opening with a smaller diameter than the proximal opening of the woven retention device. In a case where the distal end of the woven retention device is open, the diameter at the distal tip may be small enough so that the push rod does not extend through the opening when pushing the woven retention device through the delivery tube and into the bone hole.

As shown in FIG. 1A, the delivery tube 160 may include a compression portion 168 at least at or near the distal end 164 of the delivery tube 160. The compression portion 168 can force the woven retention device 100' to radially contract as the woven retention device 100' is pushed through the distal opening 165 with the push rod 170. In some embodiments, the compression portion 168 may be a portion of the delivery tube 160 with an inner diameter that is smaller than an outer diameter of the woven retention device 100' when the woven retention device 100' is in a relaxed state. Further details of the compression portion 168 according to some embodiments will be discussed further below.

According to an embodiment of the method of using a kit for inserting a woven retention device into a bone, the distal opening 165 of the delivery tube 160 may be positioned at or near the opening 156 of the bone hole 150, as shown in FIG. 1B. As such, when the woven retention device 100' is pushed through the delivery tube 160 and is compressed by the compression portion 168, the woven retention device 100' can easily be inserted into the bone hole 150 due to the radially contracted state of the woven retention device 100' from the compression portion 168. For example, the contracted state of the woven retention device 100' allows it to easily enter the opening 156 without being obstructed by the periphery of the opening 156. Also, by staying at least partially contracted even after passing through the compression portion 168 and entering the bone hole 150, the woven retention device 100' can avoid obstructions in the bone hole 150 itself due to irregularities in the bone hole 150. According to some embodiments, the woven retention devices 100, 100' have a construction such that they return to their relaxed state after passing fully through the compression portion 168, the relaxed state being one in which the woven retention device 100, 100' has a diameter $d_r$ (FIG. 1B) that is larger than a diameter $d_c$ (FIG. 1C) when in the compressed state.

It is possible that the size of the bone hole 150 may prevent the woven retention devices 100, 100' from fully returning to their relaxed state if the bone hole 150 has an inner diameter that is smaller than an outer diameter of the woven retention device in the relaxed state. Nonetheless, the woven retention device 100 will be biased to expand or return to the relaxed state. In one embodiment, the woven retention device can elastically expand and/or self-expand to the relaxed state. In expanding towards the relaxed state, the woven retention device will press against the bone surface 154 of the bone hole 150. It is also possible that the bone hole 150 has an inner diameter that is larger than the outer diameter of the woven retention device in a relaxed state. In such a case, the woven retention device may not fully contact the bone surface 154 of the bone hole 150 when the woven retention device is in the relaxed state. However, the woven retention device may transition to an expanded state when a fastener is later inserted into the woven retention device. Thus, in the expanded state, the woven retention device can provide the desired interaction between the fastener and the bone hole. Therefore, according to the properties of the woven retention device and the compression portion 168 of the delivery tube 160, a system and method may be provided which allows for easy insertion of the woven retention device 100, 100' into the bone hole 150 while nonetheless ensuring the desired interaction between the woven retention device, the fastener, and the bone surface 154.

Figure 2:
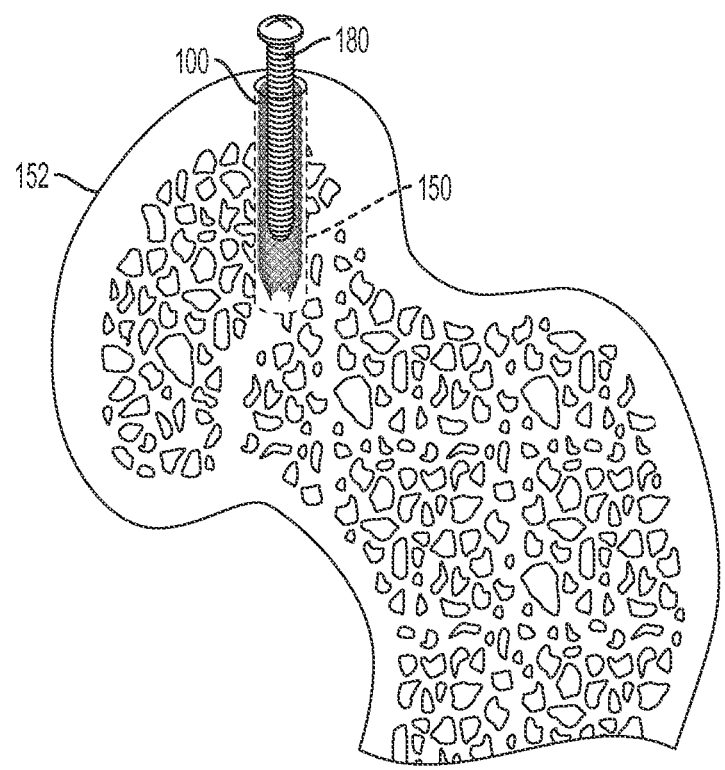
FIG. 2 shows a partial cut-away view of an implanted woven retention device with a screw being inserted after a retention device has been inserted into a bone hole, according to an embodiment of the invention.
Figure 3:
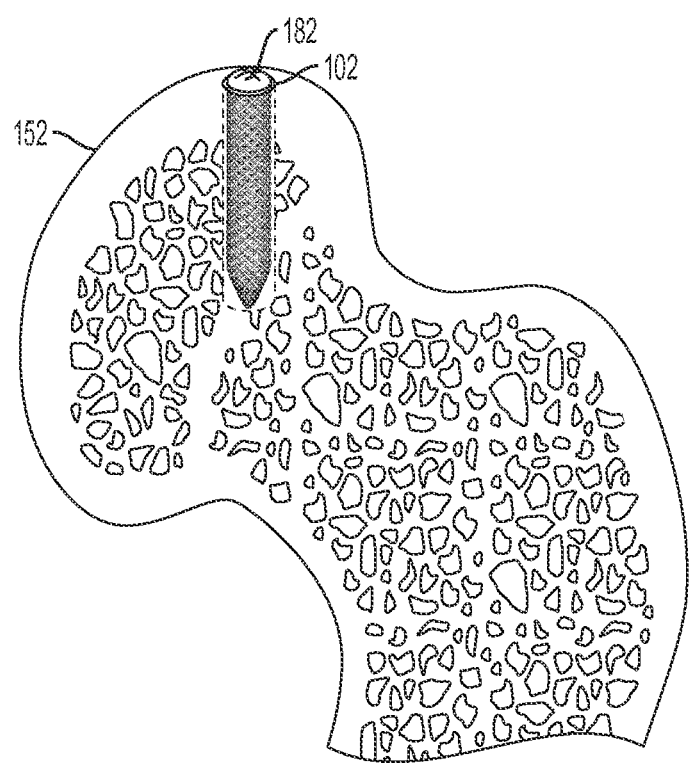
FIG. 3 shows a screw fully inserted into a woven retention device in a bone hole, according to an embodiment of the invention.

As shown in FIG. 2, the method according to some embodiments includes inserting a fastener 180 into the woven retention device 100 after the woven retention device 100 is placed into the bone hole 150. In the embodiment shown in FIG. 2, the fastener 180 is a bone screw. However, embodiments of the invention are not limited to bone screws, and other fasteners such as rods, pins, prosthetic devices, or other devices can be inserted into the woven retention device 100. As shown in FIG. 3, the fastener 180 may be inserted fully into the woven retention device 100 such that a proximal end 182 of the fastener 180 is substantially flush with the proximal end 102 of the woven retention device 100 or with the surface of the bone 152.

Figure 4:
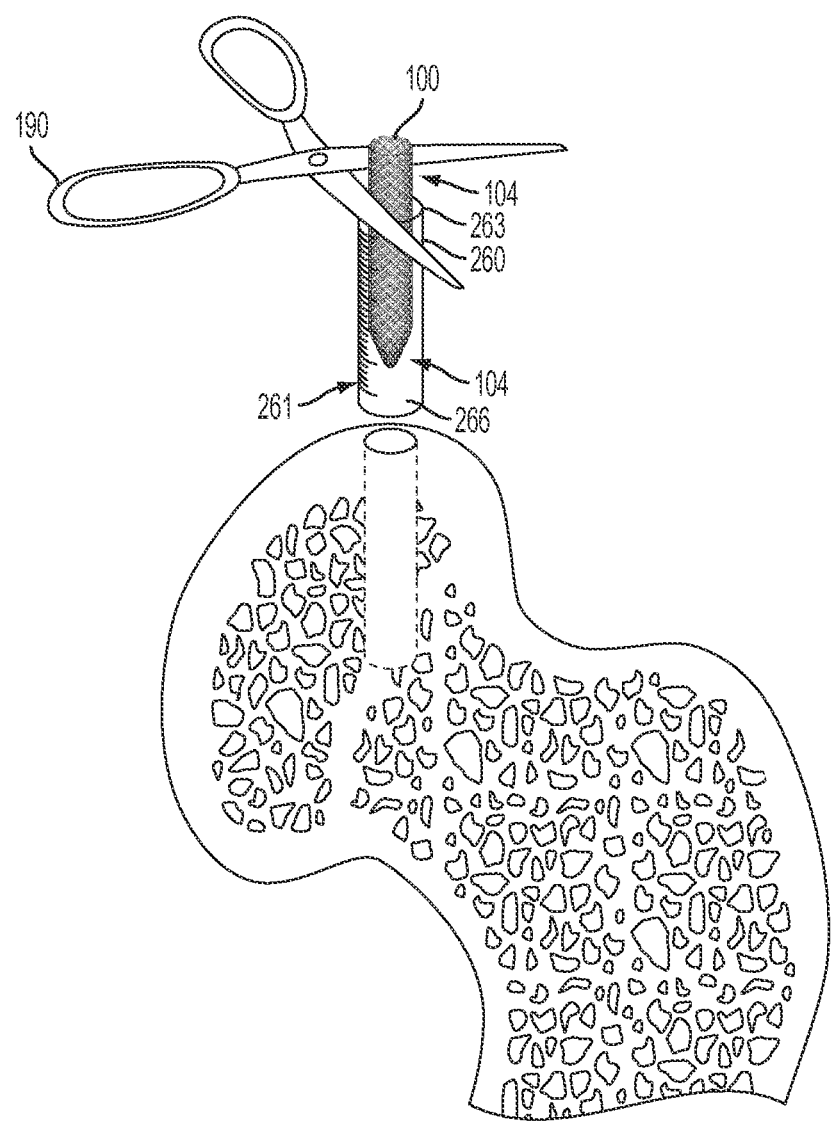
FIG. 4 shows a delivery tube having measurement indicia that allows for measuring an appropriate length of the woven retention device, and cutting the excess amount of the retention device, according to an embodiment of the invention.

According to some embodiments, a method of inserting a woven retention device may include removing an excess portion of the woven retention device 100 so that it fits as desired in a bone hole of a particular size. In this regard, embodiments include kits to aid a user or operator of the woven retention device to easily measure, cut, and insert the woven retention device. FIG. 4 shows an example of such an embodiment. The woven retention device 100 is at least partially inserted into a measuring tube 260 that is equipped with a mechanism for measuring the woven retention device 100. In this example, the measuring is accomplished using measuring indicia 261 on the side of the measuring tube 260. According to an embodiment of the method, the woven retention device 100 is at least partially inserted into the measuring tube 260 until the distal end 104 of the woven retention device 100 reaches a desired position relative to the measuring indicia 261. The relative position of the woven retention device 100 can be appreciated by the measuring tube 260 having a clear tube body 266. After the woven retention device 100 is inserted to the desired position, a portion of the distal end 104 of the woven retention device 100 may be removed using scissors 190, for example, as shown in FIG. 4. In an embodiment, the woven retention device 100 is cut at a point approximately level the proximal opening 263 of the measuring tube 260. Therefore, the measuring indicia 261 can be arranged such that the measuring indicia 261 measure a distance from the proximal opening 263 of the measuring tube 260 and, correspondingly, a length of the woven retention device 100 from the distal end 104 of the woven retention device 100 to proximal opening 263 (or other position where the woven retention device 100 is cut).

Figure 5A:
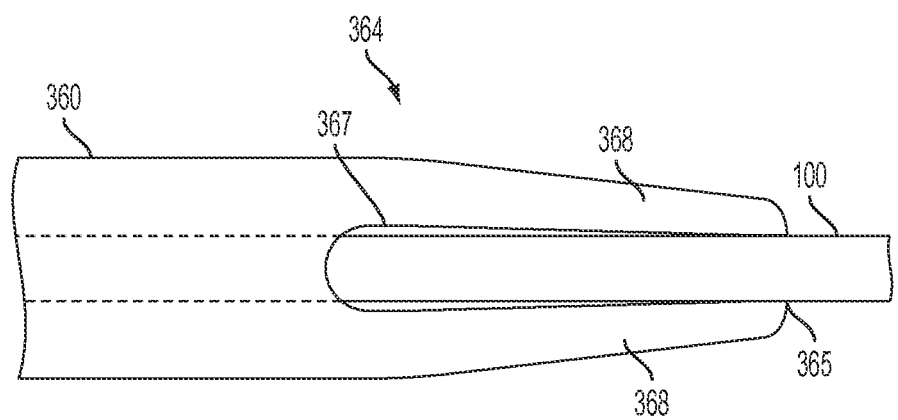
FIG. 5A shows a woven retention device becoming compressed due to passing through the compression portion of the delivery tube, according to an embodiment of the invention.

According to some embodiments, a portion of the delivery tube 360 near the distal end 364 includes one or more distal slots 367 as shown in FIG. 5A. The distal slots 367 define one or more prongs 368 at or near the distal end 364 of the delivery tube 360. The compression portion of the delivery tube 360 can be formed from these compression prongs 368. For example, as shown in FIG. 5A, the compression prongs 368 are biased radially inward towards a longitudinal axis of the delivery tube 360, thus forming a narrowed distal opening 365 of the delivery tube 360.

According to some embodiments, there can be an odd number of distal slots 367 on the distal end 364 of the delivery tube 360. An odd number can provide more circumferentially uniform compression of the woven retention device because the distal slots are not aligned with each other. An even number of slits would have the slots aligned if the slots are placed symmetrically about the circumference of the delivery tube.

Figure 5B:
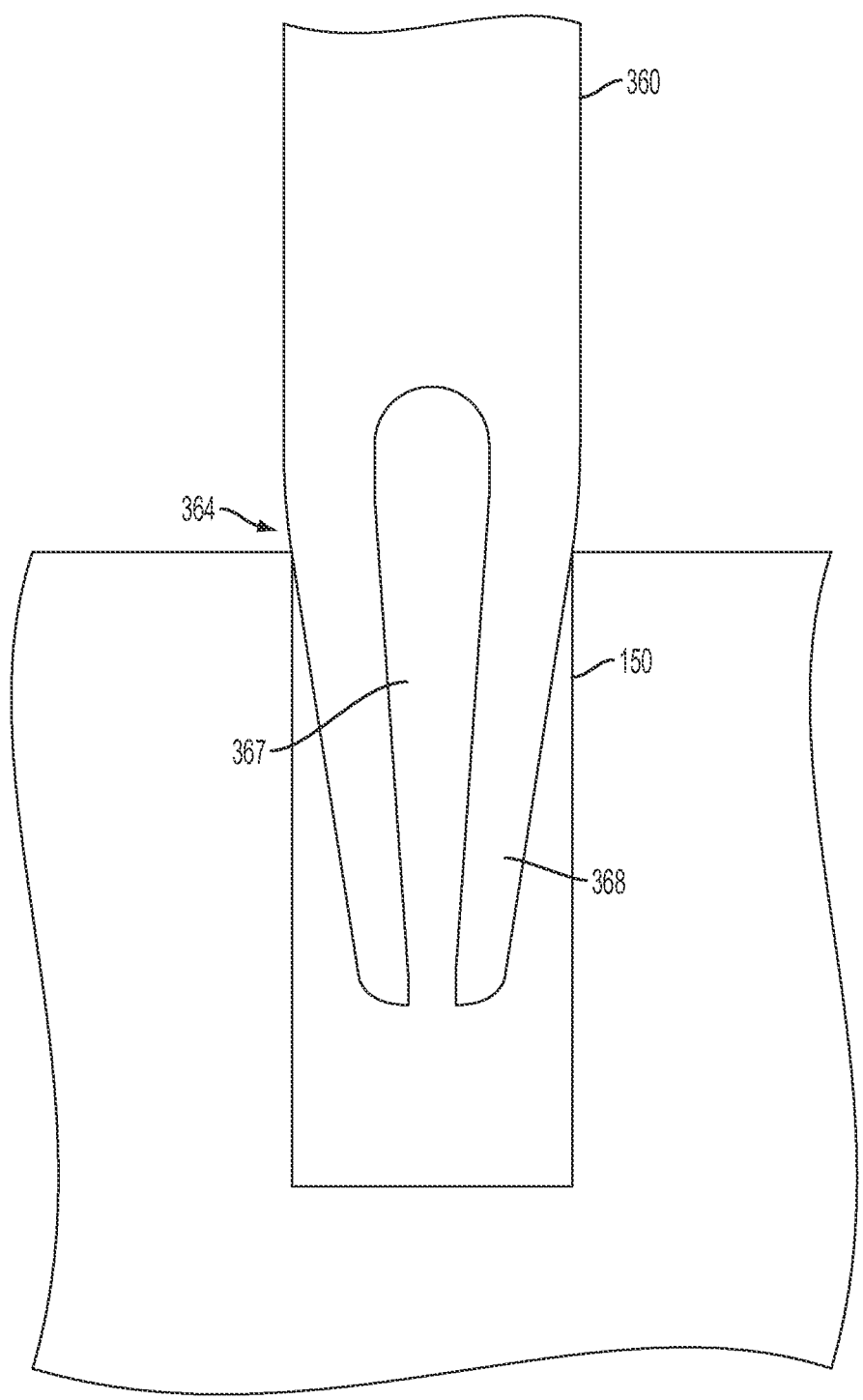
FIG. 5B shows a close-up view of delivery tube disposed partially in a bone hole, according to an embodiment of the invention.

As shown in FIG. 5B, the distal end 364 of the delivery tube 360, according to an embodiment, may be brought into closer proximity to the bone hole 150, even to the point of being partially inserted into the bone hole 150. Insertion of the distal end 364 of the delivery tube 360 can be aided by the tapering of the distal end 364 resulting from the compression prongs 368 and distal slots 367.

FIGS. 6A through 6E show an example of the delivery tube according to an embodiment. Three distal slots 467 and three compression prongs 468 are formed in the distal end 464 of the delivery tube 460. Measuring indicia 461 are visible in FIGS. 6B and 6C along the body of delivery tube 460. As shown in FIG. 6C, the delivery tube 460 also has a slotted opening (push guide 469) formed along a substantial length of the delivery tube 460. As discussed below, the push guide 469 can assist in pushing the woven retention device through the entirety of the delivery tube 460 until it woven retention device has fully exited the delivery tube 460 into the bone hole. In some embodiments, the push guide 469 is contiguous with the proximal opening at the proximal end 462 of the delivery tube 460. In other embodiments, the push guide 469 may be separated from the proximal opening on the proximal end 462. The push guide 469 can also allow an operator of the delivery tube 460 to see a position of the woven retention device through the opening. Thus, the delivery tube 460 need not be made of a transparent material for using the measuring indicia 461.

Figure 7B:
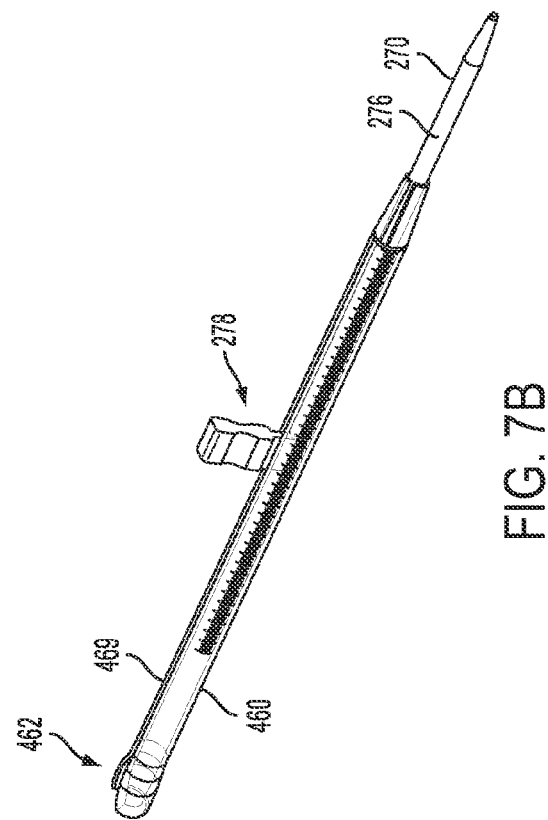
FIGS. 7A and 7B show a slidable push rod and delivery tube with a measuring scale, according to an embodiment of the invention.
Figure 7A:
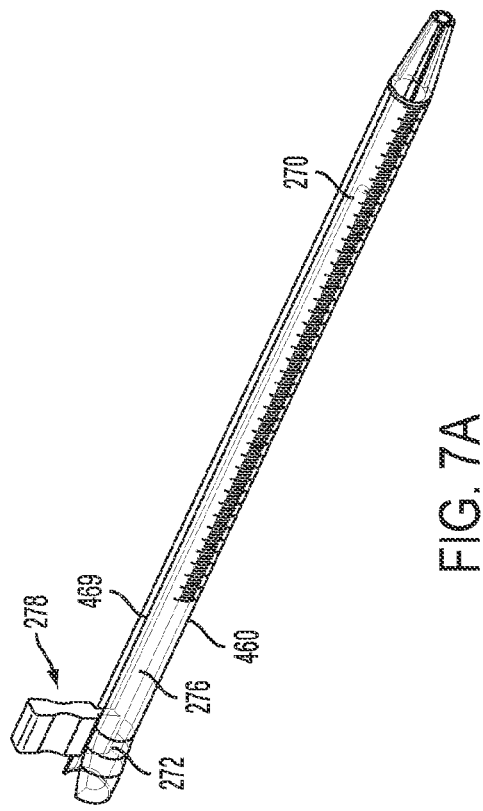

FIGS. 7A and 7B show an embodiment in which the delivery tube 460 is outfitted with a push rod 270 having a rod lever 278 on or near the proximal end 272 of the push rod 270. The rod lever 278 extends radially outward from the rod body 276 through the push guide 469. An operator of the system can slide the rod lever 278 back and/or forth in the push guide 469 so that the push rod 270 may be easily movable along a substantial length of the delivery tube 460 by an operator of the system. Therefore, the push rod 270 does not need to be long enough for the proximal end 272 of the push rod 270 to remain proximal to the proximal end 462 of the delivery tube 460 because the operator can maintain control of the push rod 270 via the push guide 469. Thus, a more compact system is provided, saving both space and material costs.

Figure 8A:
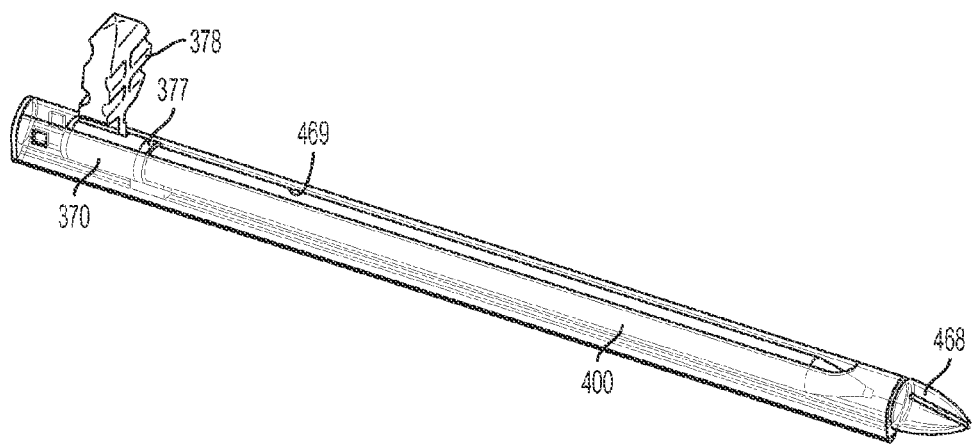
FIGS. 8A-8E show a slotted delivery tube, push rod with a planar surface handle that is perpendicular to the longitudinal axis of the delivery tube, and a stopper coupled to the push rod inside the delivery tube, according to an embodiment of the invention.
Figure 8B:
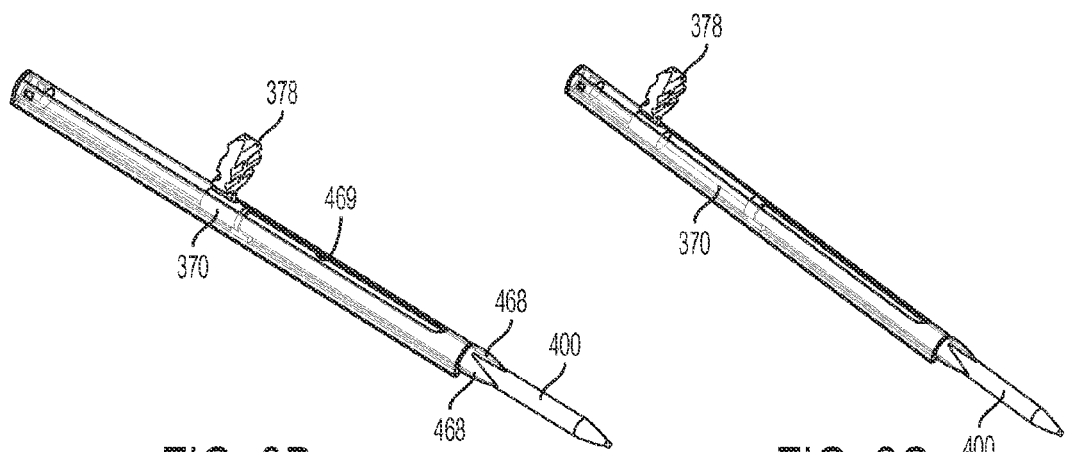
Figure 8C:
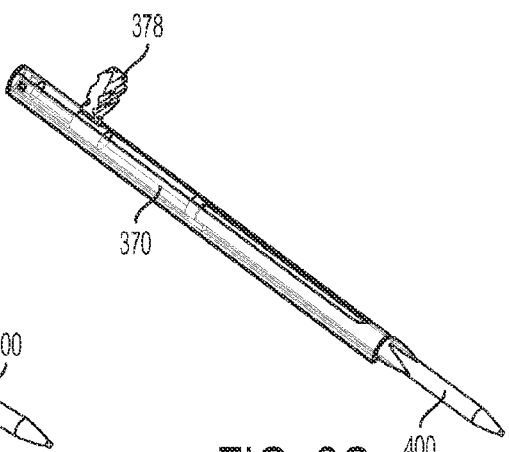
Figure 8D:
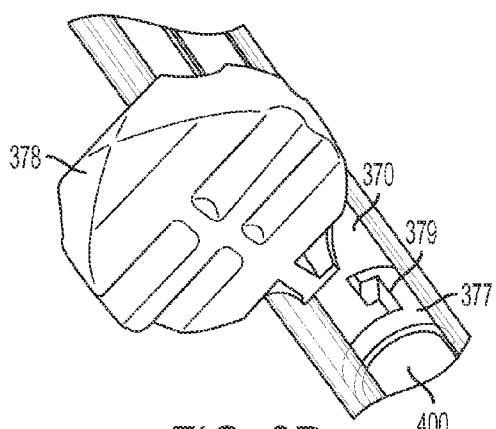
Figure 8E:
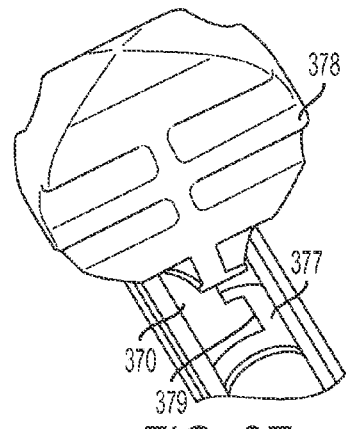

FIGS. 8A through 8E show examples of another embodiment of the kit. The woven retention device 400 is fixed to a stopper 377 to which the push rod 370 is coupled. In an embodiment, an unseen portion of the push rod 370 extends past stopper 377 to push the woven retention device 400 out of the delivery tube. Coupling between the push rod 370 and the stopper 377 is achieved by locking portion 379. The push rod 370 can be de-coupled from the stopper 377 by a rotation of the push rod 370 about its longitudinal axis. After being decoupled, the push rod 270 can be at least partially retracted from the woven retention device 400 (see FIG. 8C) so that a distal portion of the woven retention device can be cut. FIG. 8C also reveals part of the push rod 370 that was previously inside the woven retention device 400 when the push rod 370 was coupled to the stopper 377.

The rod lever 378 of the push rod 370 has a substantially planer surface that is perpendicular to the longitudinal axis of the push rod 370. FIGS. 8A-8C also show how the compression prongs 468 of the delivery tube 460 can spread apart from one another when the woven retention device 400 is being pushed through them. Thus, the compression prongs 468 can be flexible to allow the woven retention device 400 to pass through the compression prongs 468 while also radially compressing the woven retention device 400 due to the inward bias of the compression prongs 468.

Figure 9A:
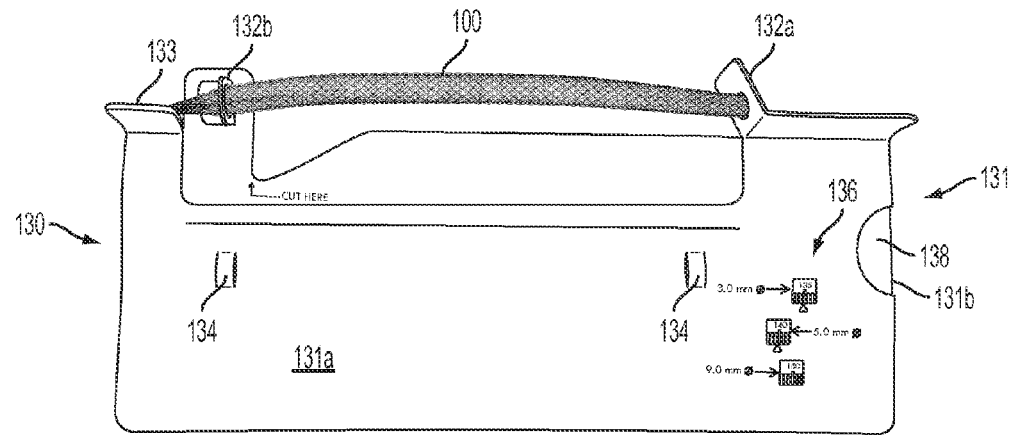
FIGS. 9A-9D show a packaging system with a slidable measuring mechanism for measuring and cutting the woven retention device, according to an embodiment of the invention.
Figure 9B:
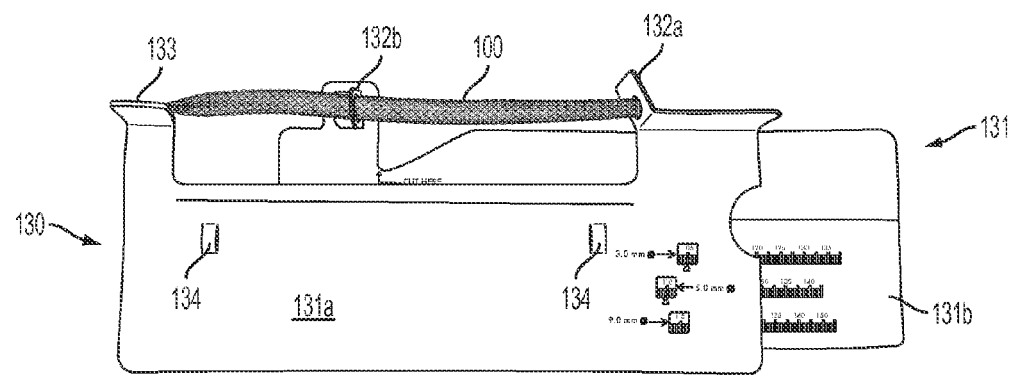
Figure 9C:
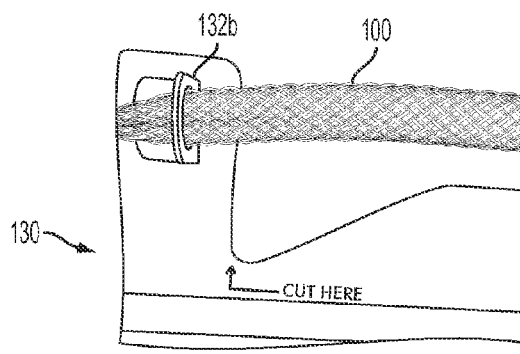

Some embodiments may include additional systems for packaging, measuring, and preparing the woven retention device for use. FIGS. 9A-9C show a packaging and preparation system for the woven retention device 100 according to an embodiment. The packaging 130 includes a backing card 131 on which the woven retention device 100 is mounted in mounting loops 132a, 132b. The backing card 131 may include two cards 131a, 131b that are movable relative to one another. The pullout card 131b may be pulled out from the stationary card 131a by pulling the pullout card 131b in the pull tab area 138. When the pullout card 131b is pulled outwardly from the stationary card 131a, the mounting loop 132b, which is attached to the pullout card 131b, also moves relative to the mounting loop 132a, which is attached to the stationary card 131a. As the pullout card 131b is moved, one or more measuring indices 140 within the measurement windows 136 will move relative to a marker 142 of the stationary card 131a. The measurement indicated by the marker 142 corresponds to a distance between a point on the woven retention device 100 indicated by a marker on the movable mounting loop 132b and the distal tip (not shown) of the woven retention device 100 that is attached at the attachment portion 133. Therefore, according to some embodiments, a user of the woven retention device 100 cut the woven retention device 100 to any desired length using the measuring system provided on the packaging of the woven retention device 100. For example, when the desired length is obtained in the measurement window 136, the user can cut the woven retention device 100 where indicated by the marker on the movable mounting loop 132b (e.g., a point indicated by the words "cut here" in FIGS. 9A-9C). After cutting, the portion of the woven retention device 100 between the attachment portion 133 and the movable mounting loop 132b may be inserted into a bone using other methods described herein.

Figure 9D:
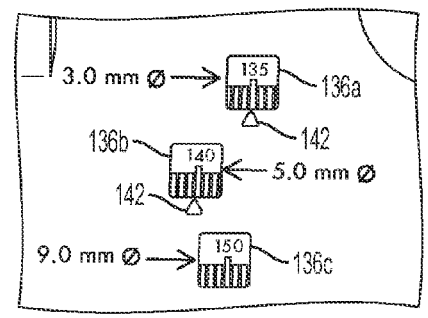

In some embodiments, multiple measurement windows 136 are provided in the packaging system 130. Each of the multiple measurement windows 136 may have measuring indices that are calibrated for woven retention devices of a certain type. For example, in an embodiment, the measurement windows 136 may each be calibrated for a woven retention device of a different size, diameter, or weave pattern. In one embodiment, as shown in FIG. 9D, the measurement windows are staggered to calibrate each set of indices to differently constructed or sized woven retention devices. For example, a first measurement window 136a may have measuring indices for a small-diameter woven retention device 100 (e.g., 3.0 mm in diameter). A second window 136b may have measuring indices for a medium-diameter woven retention device 100 (e.g., 5.0 mm in diameter). A third window 136c may have measuring indices for a large-diameter woven retention device 100 (e.g., 9.0 mm in diameter). These diameters are given as examples only. The number of measuring windows 136 provided and the diameters or other properties used to differentiate the measuring scales are not limited to these examples.

According to an embodiment, the packaging may also include mounting portions 134 for a push rod (not shown in FIGS. 9A-9C). Examples of various embodiments of the packaging and retention device systems 230a-230d are shown in FIGS. 10A-10D. The packaging system 230c is shown in more detail in FIGS. 11A and 11B. The packing system 230c has a similar construction to the embodiment shown in FIGS. 9A-9D. However, in packaging system 230c, push rod 470c is shown mounted in a push rod holder portion 234. In addition, delivery tube 560c is also included in the packaging 230c, as well as two woven retention devices 300c. Packaging 230c also differs from the embodiment in FIGS. 9A-9D because a movable mounting and cutting guide 232 extends over both woven retention devices so that both can optionally be measured and/or cut at the same time. The distal end 304c is arranged on an opposite end of the woven retention devices 300c, so the measuring indicia in measurement windows 136 correspond to a length between the distal end 304c and the position of the movable mounting and cutting guide 232.

In some embodiments, as shown in packaging systems 230a and 230b, the woven retention devices 300a, 300b can be packaged within the delivery tubes 560a, 560b, respectively. This results in compact packaging and, in some embodiments, a woven retention device that can be immediately deployed from the delivery tube. Alternatively, even when packaged within the delivery tube, the woven retention device can be at least partially removed from the delivery tube for measuring and cutting. The push rod 470a also has a bent portion 479, which will be discussed further with respect to FIGS. 13-15.

Also in FIG. 10, packaging system 230d shows an embodiment in which a delivery tube 560d is packaged with a straight push rod 470d. The delivery tube 560d and push rod 470d may be reusable, while the woven retention device is not reusable because they are implanted into the patient. Thus, it is contemplated that, in some embodiments, the woven retention device can be packaged separately from the delivery tube and/or push rod. Alternatively, the woven retention device can be packaged with one or both of the delivery tube and the push rod. When the woven retention device is included in the package with the delivery tube, the woven retention device can be pre-inserted into the delivery tube. By packaging the woven retention device within the delivery tube, a user of the system can avoid the step of inserting the woven retention device into the delivery tube.

FIGS. 11A and 11B show close-up views of packaging system 230c according to one embodiment. The measurement windows 136 include two windows for two different scales: 136', 136" for woven retention devices with diameters of 5.0 mm and 9.0 mm. respectively. Although a third measurement window is shown, no measuring indices are provided for that window in the example shown. However, measurement windows 136' and 136" may be used for a different measuring scale corresponding to a woven retention device having a diameter of 3.0 mm, for example. It is contemplated that the two woven retention devices 300c' and 300c" can have two different diameters, corresponding to the scales used in measurement windows 136' and 136". Thus, in FIGS. 11A and 11B, woven retention device 300c' may have a diameter of 5.0 mm, and woven retention device 300c" may have a diameter of 9.0 mm. The two separate lines of measuring indices 240 can be seen more clearly in FIG. 11B, which is shown with the pull out card 232b partially pulled apart from the stationary card 231a.

Figure 10D:
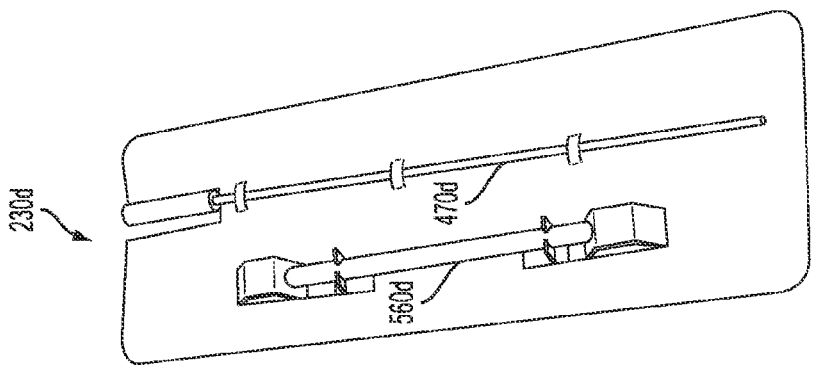
FIGS. 10A-10D show multiple packaging, delivery tubes and push rod embodiments, according to embodiments of the invention.
Figure 10C:
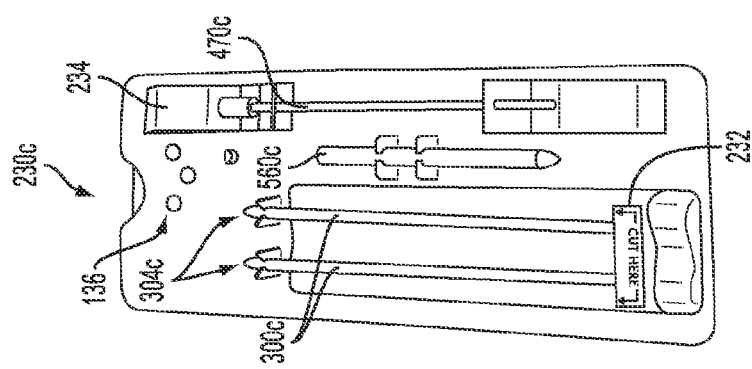
Figure 10B:
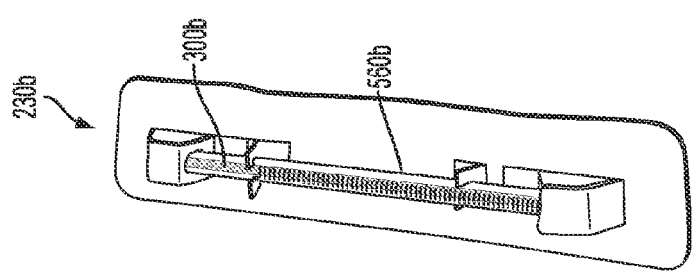
Figure 12:
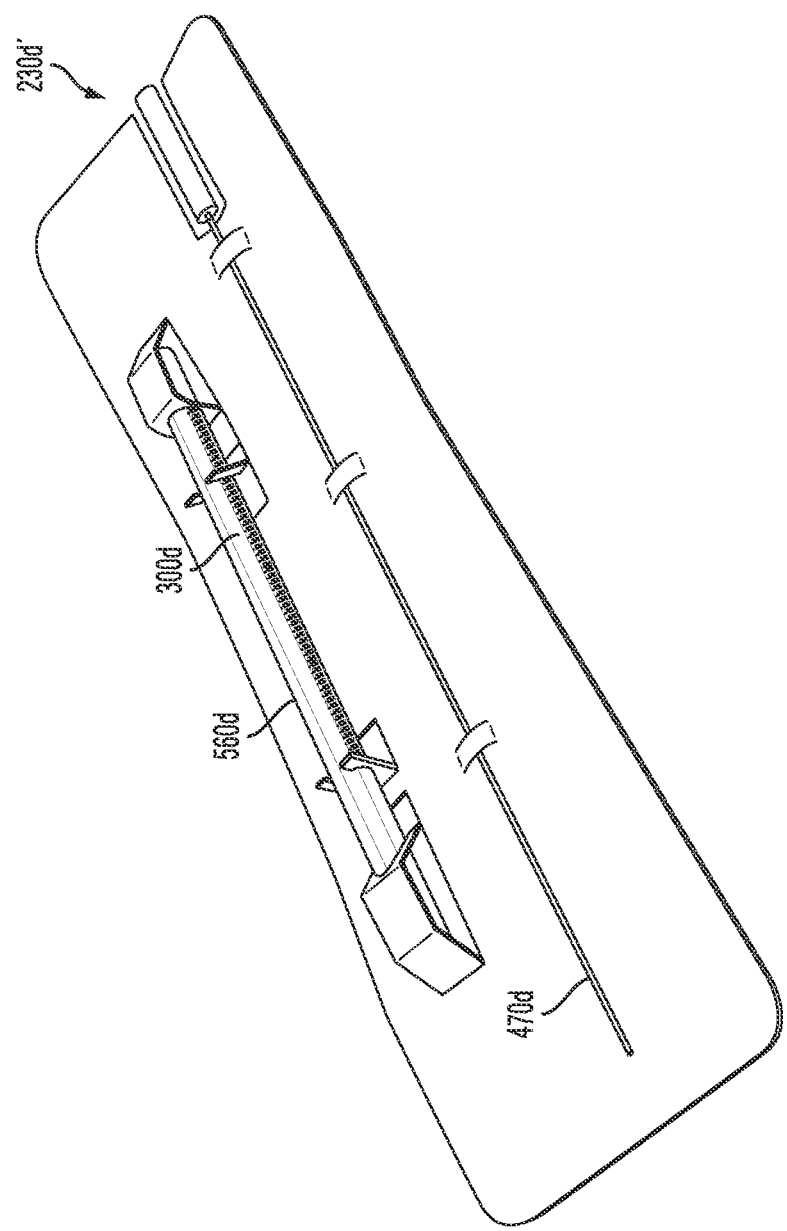
FIG. 12 shows packaging elements of the woven retention device kit in a long form of the push rod, according to an embodiment of the invention.

FIG. 12 shows a variation on the embodiment of the packaging system 230d from FIG. 10D. In FIG. 12, packaging system 230d' includes delivery tube 560d, and push rod 470d, as well as woven retention device 300d being pre-loading in the delivery tube 560d. Because no push guide 469 is providing along the side wall of the delivery tube 560d, the push rod 470d in the embodiment shown must be long enough to at least extend from one side of the delivery tube 560d to the other side in order to push the woven retention device 300d out of the delivery tube 560d and into a bone of a patient. This long push rod 470d results in a larger overall package.

Figure 10A:
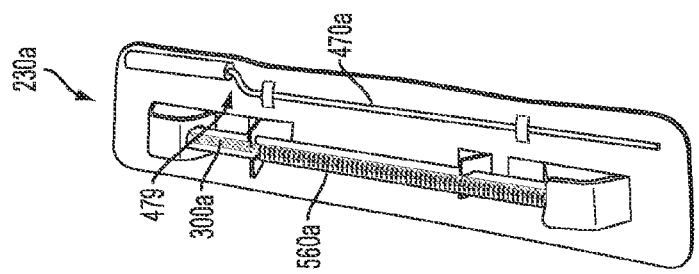
Figure 13:
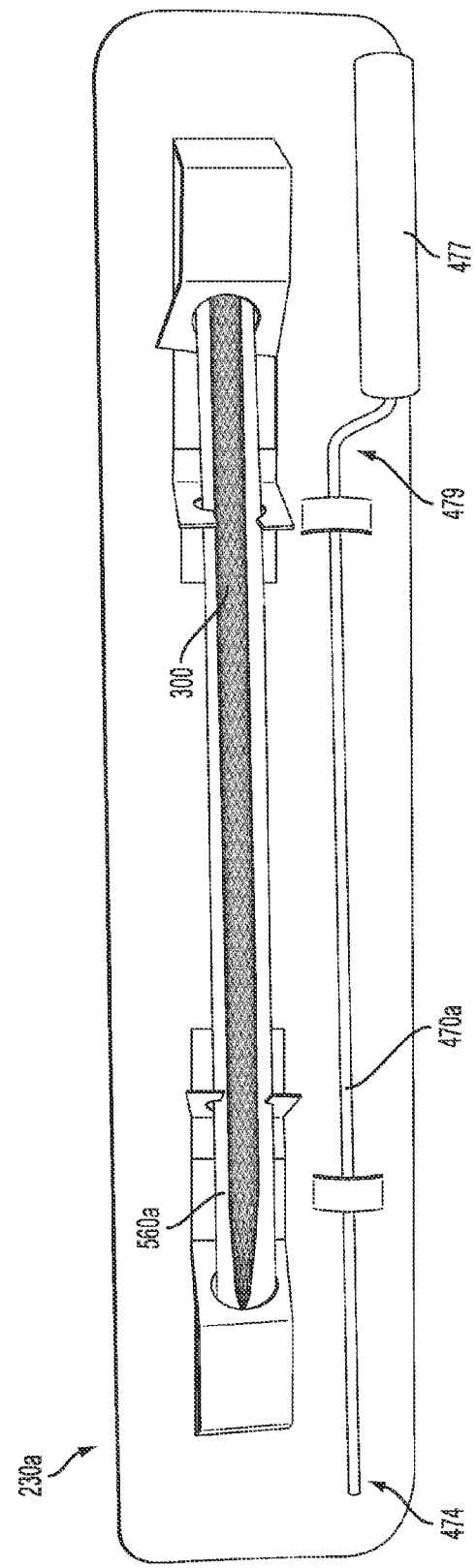
FIG. 13 shows packaging elements of the woven retention device kit with a push rod having an offset handle portion, according to an embodiment of the invention.
Figure 14:
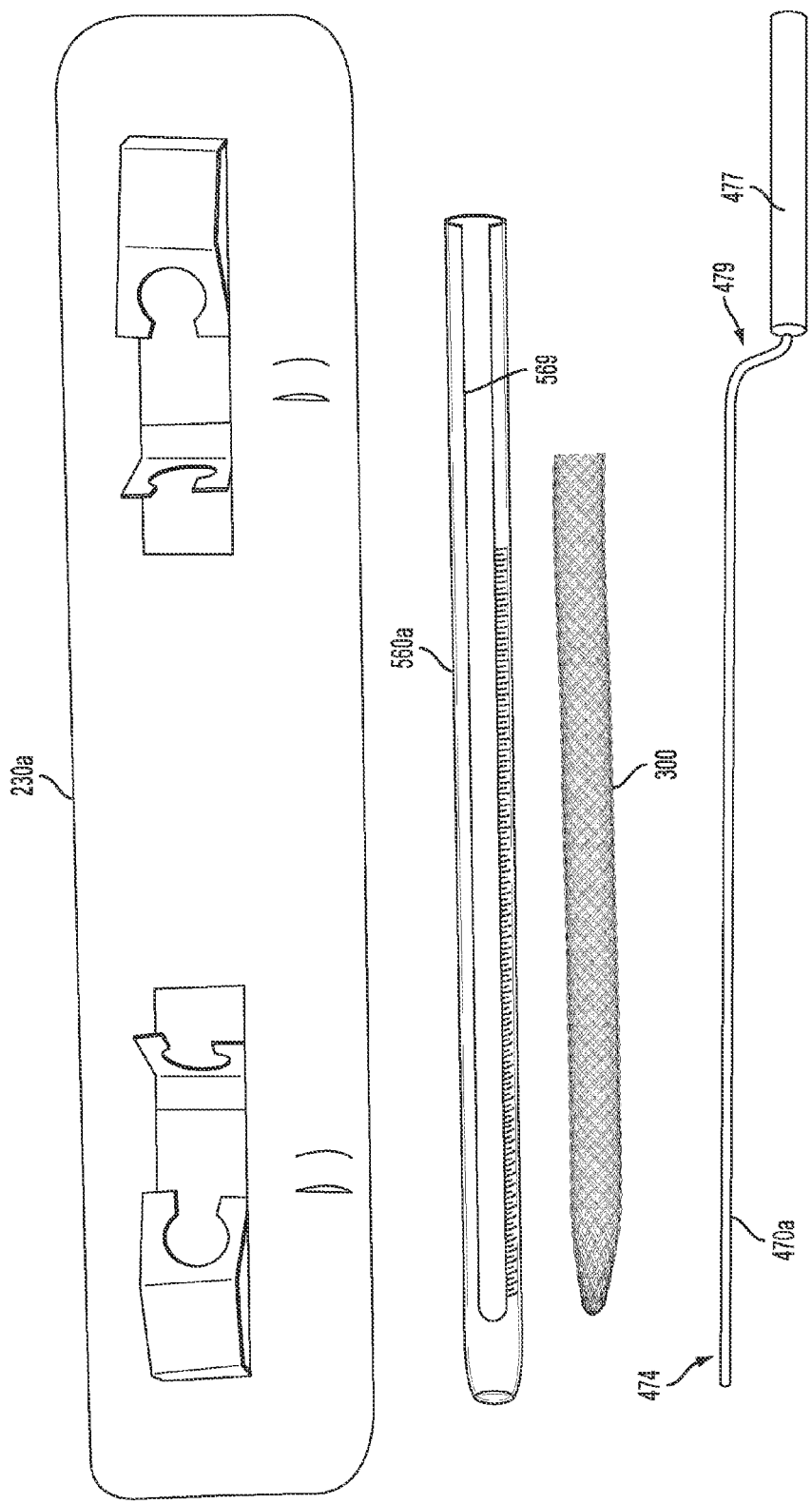
FIG. 14 shows separated elements of the woven retention device kit shown in FIG. 13, according to an embodiment of the invention.
Figure 15:
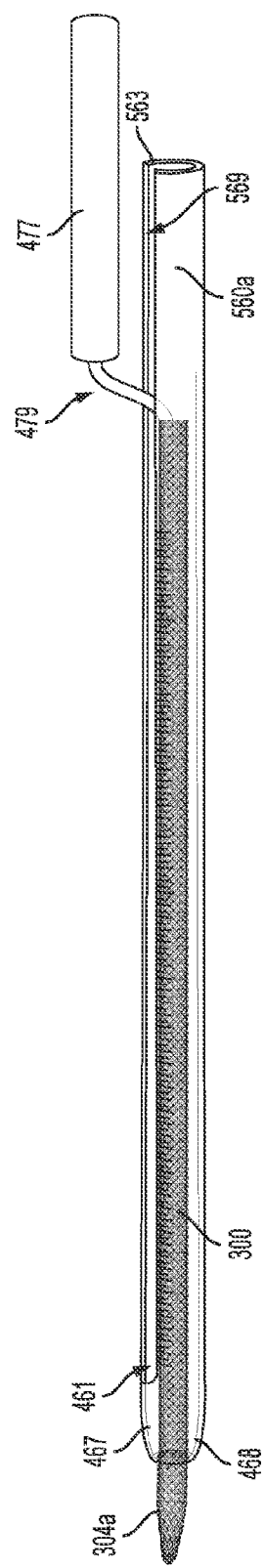
FIG. 15 shows the elements of the woven retention device kit of FIG. 13 in an arrangement for inserting the woven retention device into a bone, according to an embodiment of the invention.

In contrast, according to the embodiment shown in FIG. 10A as packaging system 230a, and the embodiments shown in FIGS. 13-15, a delivery tube 560a with a push guide 569, as shown in FIG. 14, can provide an overall shorter package 230a and push rod 470a that is shorter in length. The push rod 470a does not necessarily have to be longer than the delivery tube 560a, because the push guide 569 allows the push rod 470a to slide down the length of the delivery tube 560a. The bent portion 479 of the push rod 470a allows the handle 477 to remain outside of the delivery tube 560a while the distal end 474 of the push rod 470a pushes the woven retention device 300 inside the delivery tube 560a.

The push guide 569 can be seen more clearly in FIG. 14, where the components of packaging system 230a are separated. In some embodiments, the push guide 569 may extend over only part of the length of the delivery tube 560a. In this way, the push rod 470a may be prevented from all the way through the distal opening 565a of the delivery tube 560a. However, it is possible that the push guide 569 may extend over the entire length of the delivery tube 560a in some embodiments. The length of the push guide 569 may be coordinated with the placement and length of the measuring indicia 461 so that the woven retention device 300 can be measured using the entire range of the measuring indicia 461 based on the distance the woven retention device 300 can be pushed by the push rod 470a.

FIG. 15 shows an embodiment of the parts from FIGS. 13 and 14 as they are used to push the woven retention device 300 through the delivery tube 560a. The distal end 304a of the woven retention device 300 is shown protruding from the delivery tube 560a, as the woven retention device 300 passes through the compression prongs 468 formed by the distal slots 467. Due to the bent portion 479 of the push rod and the push guide 569, the handle 477 is able to extend beyond the proximal opening 563 of the delivery tube 560a, on an outside of the delivery tube 560a. Thus, the embodiment shown in FIG. 15 provides a compact and sufficient kit and method of inserting a woven retention device into a bone.

The foregoing descriptions include examples of embodiments of the woven retention devices and tools for using and inserting the woven retention devices. However, variations in these devices and system are contemplated within the scope of the invention. For example, in some embodiments, the distal tip of the woven retention devices may be closed, while in other embodiments the distal tip may have an opening with a smaller diameter than the proximal opening of the woven retention device.

EXAMPLES

The following is provided as an example of sizes and dimensions of a delivery tube and push rod according to an example of one embodiment of the invention. However, embodiments are not limited to the following dimensions.

The push rod may be formed of stainless steel (e.g., 316 SS). In an embodiment where the push rod is formed without the bent portion 479, the push rod may have an overall length of 300 mm, where a handle portion of the push rod may be about 50 mm long and the elongated arm that is inserted into the delivery tube and woven retention device may be 250 mm. In an embodiment where the push rod is formed with the bent portion 479, the overall length may be shorter. The elongated are may have a diameter of about 2 mm. The diameter of the elongated arm may be smaller or larger, as long as the elongated arm is able to slide within the delivery tube and push the woven retention device. The handle portion may have a diameter of 8 mm, for example.

The delivery tube may have an overall length of about 180 mm. If a push guide is formed in the side of the delivery tube, then the push guide may extend for about 160 mm along the length of the delivery tube. A length of the compression prongs and end slots formed in the delivery tube may be about 15 mm. The outer diameter of the delivery tube may be about 8.5 mm, and an inner diameter may be about 7 mm. The distal opening formed at the tip of the compression prongs may have a diameter of 2.5 mm. This diameter may expand as the woven retention device is pushed through the flexible compression prongs, in some embodiments. The measurement scale of the measuring indices on the delivery tube may be spaced about 0.5 mm apart, in one example.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A kit for implanting a woven retention device into bone, the kit comprising:
   a woven retention device having a distal end that is tapered to a distal tip, a proximal end configured to receive a fastener, and a sleeve body between the distal and proximal ends;
   a delivery tube including a distal opening and a proximal opening, the delivery tube having a compression portion over at least a distal end of the delivery tube; and
   a push rod configured to be slideably received within the delivery tube and having a distal end configured to push the woven retention device through the distal opening of the delivery tube,
   wherein the compression portion comprises a narrowed region at or near the distal opening of the delivery tube, the narrowed region having an inner diameter that is less than a first outer diameter of the sleeve body.

2. The kit according to claim 1, wherein the woven retention device is configured to radially compress to a compressed state when at least part of the sleeve body is within the compression portion, and
   wherein the sleeve body has the first outer diameter in an uncompressed state and a second outer diameter in the compressed state, the second outer diameter being smaller than the first outer diameter.

3. The kit according to claim 1, wherein:
   the delivery tube comprises a side wall opening extending longitudinally along at least a portion of the delivery tube, and
   the push rod is arranged such that at least a portion of the push rod extends outside of the delivery tube through the side wall opening during at least a portion of a progression of the distal end of the push rod inside the delivery tube.

4. The kit according to claim 1, wherein the compression portion comprises a plurality of end slots in the delivery tube at a distal portion of the delivery tube.

5. The kit according to claim 4, wherein the plurality of slots comprises an odd number of end slots at the distal portion of the delivery tube.

6. The kit according to claim 4, wherein the compression portion further comprises a plurality of prongs disposed between slots of the plurality of slots, the prongs being configured to compress the woven retention device as the woven retention device is advanced through the distal opening.

7. The kit according to claim 2, wherein the woven retention device is configured to be expanded to a relaxed state from the compressed state.

8. The kit according to claim 7, wherein the woven retention device is configured to be expanded by self-expanding the woven retention device.

9. The kit according to claim 1, further comprising a fastener configured to be disposed within the woven retention device when the woven retention device is within the bone hole.

10. The kit according to claim 1, further comprising a measuring device arranged to measure a desired length of the woven retention device to be inserted into the bone hole.

11. The kit according to claim 10, further comprising a cutting device configured to cut the woven retention device based on the desired length measured by the measuring device.

12. The kit according to claim 10, wherein the measuring device comprises indicia arranged to indicate a distance from the distal tip of the woven retention device to a reference point, the reference point being a point at which the woven retention device is able to be cut to achieve the desired length.

13. The kit according to claim 12, wherein the indicia are arranged on a wall of the delivery tube.

14. The kit according to claim 13, wherein the designated cutting point is the proximal opening of the delivery tube.

15. The kit according to claim 12, further comprising a package containing at least one of the woven retention device, the delivery tube, and the push rod.

16. The kit according to claim 15, wherein:
the package contains the woven retention device,
the indicia are arranged on the package, and
the woven retention device is mounted on the package in a predetermined relationship relative to the indicia.

17. The kit according to claim 15, wherein:
the package further contains the delivery tube, and
the woven retention device is pre-loaded within the delivery tube.

18. The kit according to claim 15, wherein the package comprises:
a mounting surface to which the woven retention device is mounted,
a measuring surface including at least one set of measuring indicia, the measuring surface being slidable relative to the mounting surface, and
a cutting indicator fixed to the measuring surface, the cutting indicator being configured to indicate a location on the woven retention device where cutting is to be performed.

19. The kit according to claim 18, wherein the measuring surface is slidably received within an envelope comprising the mounting surface.

20. The kit according to claim 18, wherein the measuring surface includes at least one window through which the at least one set of measuring indicia are viewable, the at least one window being arranged to indicate a distance from the distal tip of the woven retention device to the location where the cutting indicator indicates the cut is to be performed.

21. The kit according to claim 18, wherein the at least one set of measuring indicia includes a plurality of sets of measuring indicia, each set of the plurality of sets of measuring indicia being calibrated based on a diameter of the woven retention device when the woven retention device is in a relaxed state.

22. The kit according to claim 1, wherein the delivery tube has a tube body extending between the proximal opening and the distal opening.

23. A kit for implanting a woven retention device into bone, the kit comprising:
a woven retention device having a distal end that is tapered to a distal tip, a proximal end configured to receive a fastener, and a sleeve body between the distal and proximal ends;
a delivery tube including a distal opening and a proximal opening, the delivery tube having a compression portion over at least a distal end of the delivery tube;
a push rod configured to be slideably received within the delivery tube and having a distal end configured to push the woven retention device through the distal opening of the delivery tube; and
a measuring device arranged to measure a desired length of the woven retention device to be inserted into the bone hole, the measuring device comprising indicia arranged to indicate a distance from the distal tip of the woven retention device to a reference point, the reference point being a point at which the woven retention device is able to be cut to achieve the desired length; and
a package containing the woven retention device, wherein the indicia are arranged on the package, and the woven retention device is mounted on the package in a predetermined relationship relative to the indicia.

24. A kit for implanting a woven retention device into bone, the kit comprising:
a woven retention device having a distal end that is tapered to a distal tip, a proximal end configured to receive a fastener, and a sleeve body between the distal and proximal ends;
a delivery tube including a distal opening and a proximal opening, the delivery tube having a compression portion over at least a distal end of the delivery tube;
a push rod configured to be slideably received within the delivery tube and having a distal end configured to push the woven retention device through the distal opening of the delivery tube;
a measuring device arranged to measure a desired length of the woven retention device to be inserted into the bone hole; and
a package comprising
a mounting surface to which the woven retention device is mounted,
a measuring surface including at least one set of measuring indicia, the measuring surface being slidable relative to the mounting surface, and
a cutting indicator fixed to the measuring surface, the cutting indicator being configured to indicate a location on the woven retention device where cutting is to be performed.

* * * * *